US008617870B2

(12) United States Patent
Matar et al.

(10) Patent No.: US 8,617,870 B2
(45) Date of Patent: Dec. 31, 2013

(54) ANTIOXIDANT PRODUCING BACTERIUM AND USES THEREOF

(75) Inventors: Chantal Matar, New Brunswick (CA); Luc J. Martin, New Brunswick (CA)

(73) Assignee: University of Ottawa, Ottawa, Ontario (CA)

(*) Notice: Subject to any disclaimer, the term of this patent is extended or adjusted under 35 U.S.C. 154(b) by 1767 days.

(21) Appl. No.: 10/548,739

(22) PCT Filed: Mar. 15, 2004

(86) PCT No.: PCT/CA2004/000389
§ 371 (c)(1),
(2), (4) Date: Aug. 24, 2006

(87) PCT Pub. No.: WO2004/101776
PCT Pub. Date: Nov. 25, 2004

(65) Prior Publication Data
US 2007/0031517 A1 Feb. 8, 2007

Related U.S. Application Data

(60) Provisional application No. 60/453,939, filed on Mar. 13, 2003.

(51) Int. Cl.
*C12N 1/20* (2006.01)
(52) U.S. Cl.
USPC .............. 435/252.1; 424/725; 424/93.4
(58) Field of Classification Search
None
See application file for complete search history.

(56) References Cited

U.S. PATENT DOCUMENTS

| 5,498,412 | A | 3/1996 | Fujie |
| 5,932,623 | A | 8/1999 | Tanabe et al. |
| 5,994,413 | A | 11/1999 | Tanabe et al. |
| 6,312,745 | B1 | 11/2001 | Durance et al. |
| 6,620,452 | B1 | 9/2003 | Haddad et al. |
| 6,676,978 | B1 | 1/2004 | Nair |
| 2002/0068102 | A1 | 6/2002 | Su et al. |
| 2002/0168429 | A1 | 11/2002 | Mann |
| 2003/0003120 | A1 | 1/2003 | Gaudout et al. |
| 2003/0008048 | A1 | 1/2003 | Winston et al. |
| 2003/0031734 | A1 | 2/2003 | Rosen |
| 2010/0092583 | A1 | 4/2010 | Matar et al. |

FOREIGN PATENT DOCUMENTS

WO WO 02/17732 A2 3/2002

OTHER PUBLICATIONS

Lindow et al. (Phytopathology, vol. 88, No. 11, 1998, pp. 1149-1157).*
O'Connor et al. (International Journal of Food Microbiology 25 (1995) 51-61).*
Onning et al., International Journal of Food Sciences and Nutrition, 1465-3478, vol. 54, Issue 4, 2003, pp. 281-289.*
Spröer et al.(International Journal of Systematic Bacteriology (1999), 49, 1433-1438).*
Day, N.B., et al., "Modified Atmosphere Packaging of Blueberries: Microbiological Changes," *Can. Inst. Food. Sci. Technol. J.* 23:59-65, Canadian Institute of Food Science and Technology (1990).
Martin, L.J., "Augmentation de la Teneur en Composés Phénoliques et de la Capacité Antioxydante du Bleuet Fermenté," Départment de Chimie et Biochimie, Faculté des Sciences, Université de Moncton, Moncton, CA, 65 pages (Sep. 2003).
Matar, C., et al., "Maximizing Phenol Yield from Wild Blueberry Fruit Through Fermentation and Bio-Transformation," Department of Agriculture, Fisheries, and Aquaculture, Adaptive Research Abstracts 1999, available online at http://web.archive.org/web/20030302011920/www.gnb.ca/0389/1999/017903036e.html, 1 page, NBDAFA (1999).
Pinhero, R.G. and Paliyath, G., "Antioxidant and Calmodulin-Inhibitory Activities of Phenolic Components in Fruit Wines and Its Biotechnological Implications," *Food Biotechnol.* 15:179-192, Marcel Dekker, Inc. (2001).
EMBL Database, Accession No. SPR233435, Sproeer, C. (first available and last updated 1999).
EMBL Database, Accession No. U88435, Whitney, A.M. (first available 1997 and last updated 1998).
EMBL Database, Accession No. U90758, Whiteney, A.M. (first available 1997 and last updated 1998).
International Search Report for International Application No. PCT/CA2004/000389, mailed Oct. 1, 2004.
Chambers, B.K., et al., "Can cranberry supplementation benefit adults with type 2 diabetes?," *Diabetes Care* 26: 2695-2696, American Diabetes Association, United States (2003).
Haddad, P.S., et al. "Comparative study on the medicinal plants most recommended by traditional practioners in Morocco and Canada," *J. Herbs, Spices. Med. Plants* 10: 25-45, The Haworth Press, Inc., England (2003).
Holzapfel, W. H, et al., "Taxonomy and important features of probiotic microorganisms in food and nutrition," *Am. J. Clin. Nutr.* 73(suppl): 365S-373S, American Society for Clinical Nutrition, United States (2001). Kähkönen, M.P., et al., "Berry Phenolics and Their Antioxidant Activity," *J. Agric. Food Chem.* 49: 4076-4082, American Chemical Society, United States (2001).
Kalt, W., et al., "Anthocyanin content and profile within and among blueberry species," *Can. J. Plant Sci.* 79: 617-623, Agricultural Institute of Canada, Canada (1999).
Kolbert, C.P. & Persing, D.H., "Ribosomal DNA sequencing as a tool for identification of bacterial pathogen," *Curr. Opin. Microbiol.* 2: 299-305, Elsevier Science Ltd., Holland (1999).

(Continued)

*Primary Examiner* — Irene Marx
(74) *Attorney, Agent, or Firm* — Sterne, Kessler, Goldstein & Fox P.L.L.C.

(57) ABSTRACT

Bacterial strains are provided that can be isolated from the microflora of lowbush blueberry (*Vaccinium angustifolium*), and that are capable of increasing the antioxidant content of their growth medium. The bacteria can be used, for example, to increase the antioxidant content of various foodstuffs, as probiotics or as additives to animal feed. Antioxidant-enriched compositions produced by fermentation processes utilizing the bacteria are also provided. The antioxidant-enriched compositions can be used in the preparation of cosmetics and nutritional supplements. The antioxidant-enriched compositions also have therapeutic applications.

10 Claims, 11 Drawing Sheets

(56) References Cited

OTHER PUBLICATIONS

Matar, C., et al., Immunomodulating effects of milks fermented by *Lactobacillus helveticus* and its non-proteolytic variant, *J. Dairy. Res.* 68: 601-609, Proprietors of Journal of Dairy Research, United Kingdom (2001).

Mazza, G., et al., "Anthocyanins, Phenolics, and Color of Cabernet Franc, Merlot, and Pinot Noir Wines from British Columbia," *J. Agric. Food Chem.* 47: 4009-4017, American Chemical Society, United States (1999).

Palys, T., et al., Discovery and Classification of Ecological Diversity in the Bacterial World: the Role of DNA Sequence Data, *Int. J. Syst. Bacteriol.* 47: 1145-1156, International Union of Microbiological Sciences, England (1997).

Saitou, N. & Nei, M., "The Neighbor-joining Method: A New Method for Reconstructing Phylogenetic Trees," *Mol. Biol. Evol.* 4: 406-425, The University of Chicago, United States (1987).

Schwartz, K., et al., "Investigation of plant extracts for the protection of processed foods against lipid oxidation. Comparison of antioxidant assays based on radical scavenging, lipid oxidation and analysis of the principal antioxidant compounds," *Eur. Food Res. Technol.* 212: 319-328, Springer-Verlag, Germany (2001).

Talcott, S.T. & Lee, J.-H., "Ellagic Acid and Flavonoid Antioxidant Content of Muscadine Wine and Juice," *J. Agric. Food Chem.* 50: 3186-3192, American Chemical Society, United States (2002).

Vandamme, P., et al., "Polyphasic Taxonomy, a Consensus Approach to Bacterial Systematics," *Microbiol. Reviews* 60: 407-438, American Society for Microbiology, United States (1996).

Ward, B.B., "How many species of prokaryotes are there?," *Proc. Natl. Acad. Sci.* 99:10234-10236, National Academy of Sciences, United States (2002).

Zheng, W., & Wang, S.Y., "Oxygen Radical Absorbing Capacity of Phenolics in Blueberries, Cranberries, Chokeberries, and Lingonberries," *J. Agric. Food Chem.* 51:502-509, American Chemical Society, United States (2003).

Co-pending Application, U.S. Appl. No. 12/541,714, inventors Matar et al., filed Aug. 14, 2009 (Not Yet Published).

Office Action mailed Jul. 20, 2012, for U.S. Appl. No. 12/541,714, filed Aug. 14, 2009, inventors: Matar, C. et al., U.S. Patent and Trademark Office, Alexandria, VA.

Office Action mailed Feb. 4, 2013, for U.S. Appl. No. 12/541,714, filed Aug. 14, 2009, inventors: Matar, C. et al., U.S. Patent and Trademark Office, Alexandria, VA.

\* cited by examiner

FIGURE 1

```
   1 TGGAGAGTTT GATCCTGGCT CAGATTGAAC GCTGGCGGCA GGCCTAACAC
  51 ATGCAAGTCG AGCGGTAGCA CGGGAGAGCT TGCTCTCTGG GTGACGAGCG
 101 GCGGACGGGT GAGTAATGTC TGGGAAACTG CCTGATGGAG GGGGATAACT
 151 ACTGGAAACG GTAGCTAATA CCGCATGATG TCGCAAGACC AAAGTGGGGG
 201 ACCTTCGGGC CTCACGCCAT CGGATGTGCC CAGATGGGAT TAGCTAGTAG
 251 GTGGGGTAAT GGCTCACCTA GGCGACGATC CTAGCTGGTC TGAGAGGATG
 301 ACCAGCCACA CTGGAACTGA GACACGGTCC AGACTCCTAC GGGAGGCAGC
 351 AGTGGGGAAT ATTGCACAAT GGGCGCAAGC CTGATGCAGC CATGCCGCGT
 401 GTGTGAAGAA GGCCTTAGGG TTGTAAAGCA CTTTCAGCGA GGAGGAAGGC
 451 GTTGTAGTTA ATAGCTGCAA CGATTGACGT TACTCGCAGA AGAAGCACCG
 501 GCTAACTCCG TGCCAGCAGC CGCGGTAATA CGGAGGGTGC AAGCGTTAAT
 551 CGGAATTACT GGGCGTAAAG CGCACGCAGG CGGTTTGTTA AGTCAGATGT
 601 GAAATCCCCG AGCTTAACTT GGGAACTGCA TTTGAAACTG GCAAGCTAGA
 651 GTCTTGTAGA GGGGGGTAGA ATTCCAGGTG TAGCGGTGAA ATGCGTAGAG
 701 ATCTGGAGGA ATACCGGTGG CGAAGGCGGC CCCCTGGACA AAGACTGACG
 751 CTCAGGTGCG AAAGCGTGGG GAGCAAACAG GATTAGATAC CCTGGTAGTC
 801 CACGCTGTAA ACGATGTCGA CTTGGAGGTT GTGCCCTTGA GGCGTGGCTT
 851 CCGGAGCTAA CGCGTTAAGT CGACCGCCTG GGAGTACGG CCGCAAGGTT
 901 AAAACTCAAA TGAATTGACG GGGGCCCGCA CAAGCGGTGG AGCATGTGGT
 951 TTAATTCGAT GCAACGCGAA GAACCTTACC TACTCTTGAC ATCCAGAGAA
1001 TTTGCTAGAG ATAGCTTAGT GCCTTCGGGA ACTCTGAGAC AGGTGCTGCA
1051 TGGCTGTCGT CAGCTCGTGT TGTGAAATGT TGGGTTAAGT CCCGCAACGA
1101 GCGCAACCCT TATCCTTTGT TGCCAGCACG TAAGGTGGGA ACTCAAAGGA
1151 GACTGCCGGT GATAAACCGG AGGAAGGTGG GGATGACGTC AAGTCATCAT
1201 GGCCCTTACG AGTAGGGCTA CACACGTGCT ACAATGGCGT ATACAAAGAG
1251 AAGCGAACTC GCGAGAGCAA GCGGACCTCA TAAAGTACGT CGTAGTCCGG
1301 ATTGGAGTCT GCAACTCGAC TCCATGAAGT CGGAATCGCT AGTAATCGTA
1351 GATCAGAATG CTACGGTGAA TACGTTCCCG GGCCTTGTAC ACACCGCCCG
1401 TCACACCATG GGAGTGGGTT GCAAAAGAAG TAGGTAGCTT AACCTTCGGG
1451 AGGGCGCTTA CCACTTTGTG ATTCATGACT GGGGTGAAGT CGTAACAAGG
1501 TAACCGTAGG GGAACCTGCG GTGGATCACC TCCTT
```

FIGURE 6
A
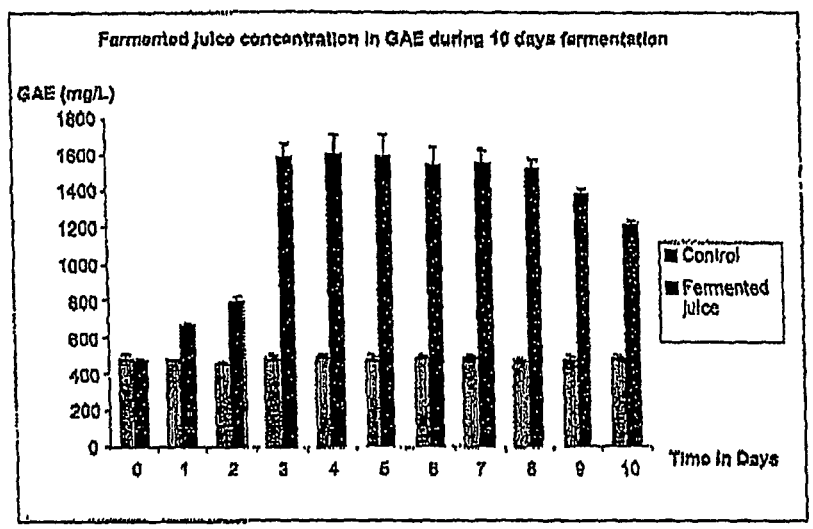
B
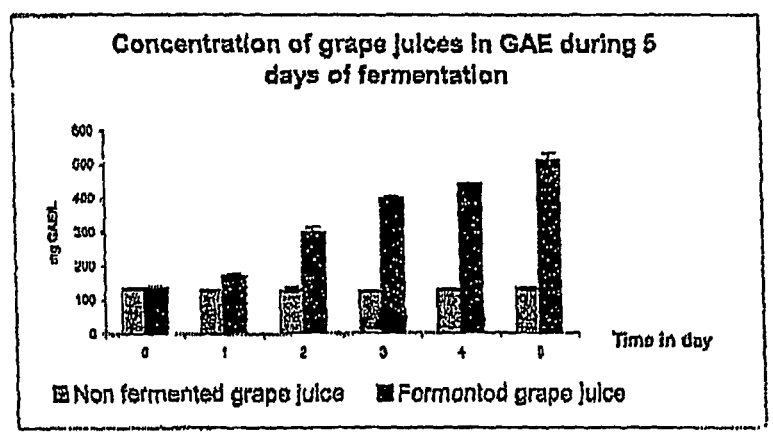

FIGURE 8
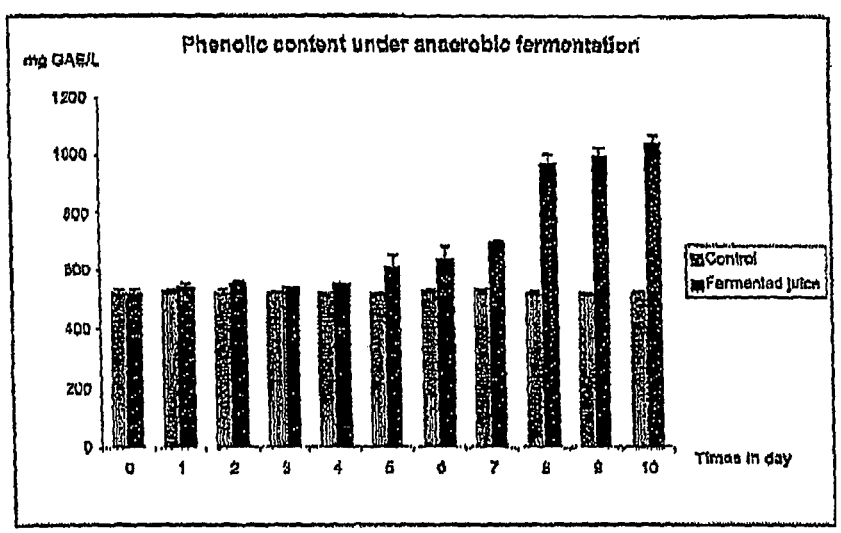
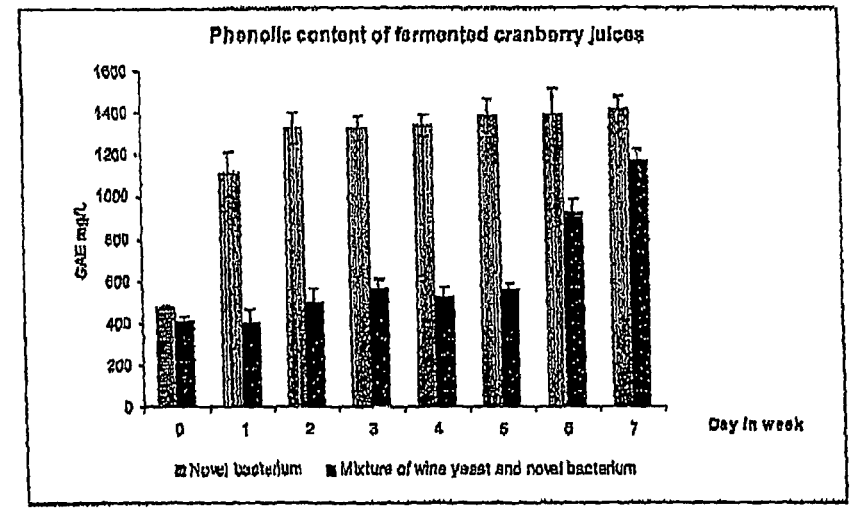

FIGURE 10
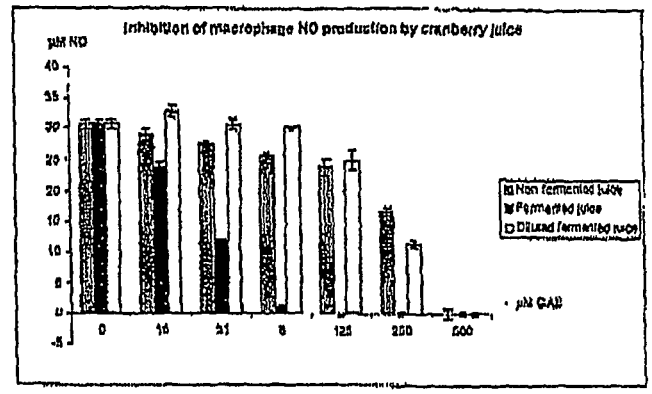
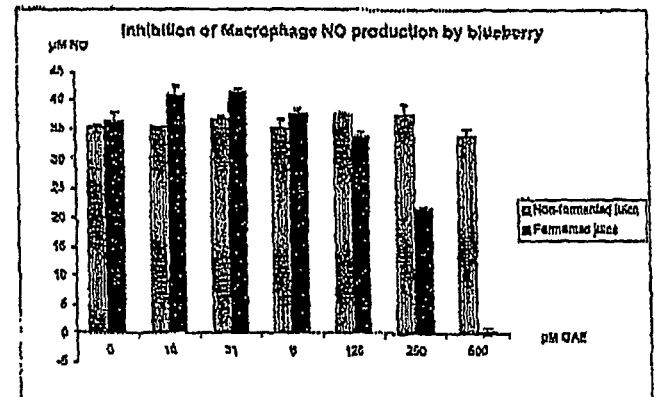
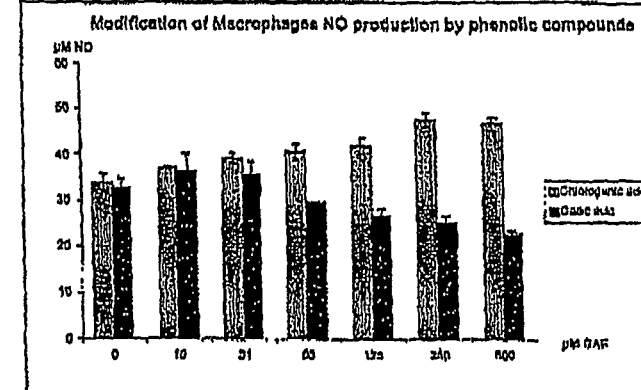

FIGURE 11
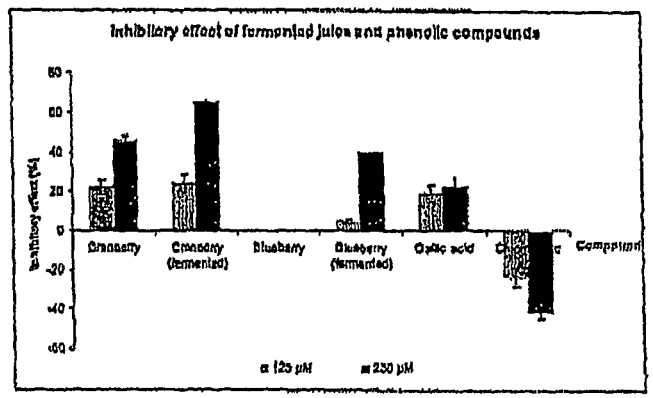
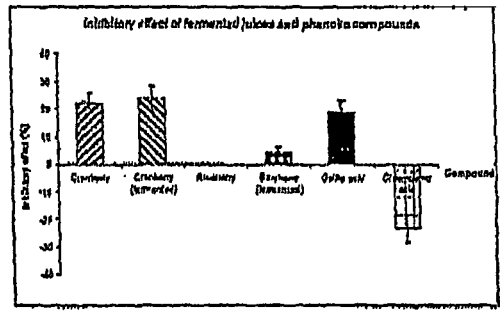
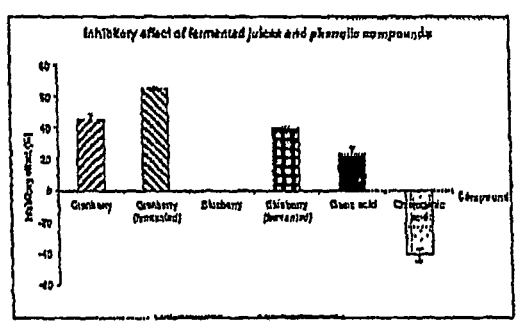

ical antioxidant compositions comprising a carrier or diluent and an antioxidant-enriched fruit extract produced by a process of the invention.

ANTIOXIDANT PRODUCING BACTERIUM AND USES THEREOF

FIELD OF THE INVENTION

The present invention pertains to the field of bacterial fermentation, in particular to an antioxidant producing bacterium and the use thereof in fermentation to produce antioxidants.

BACKGROUND OF THE INVENTION

Naturally occurring plant derived compounds are believed to afford some health benefits due in part to their antioxidant properties. These antioxidant activities may be important in preventing, treating or ameliorating many diseases, for example, cancer, neurodegenerative diseases such as Parkinson's and Alzheimer's, cardiovascular disease, and inflammation, as well as various conditions related to aging. Indeed, there is growing evidence that these compounds may be beneficial as chemopreventative, anti-inflammatory, immunomodulatory or cardioprotective agents. Accordingly, there is extensive research directed at identifying, extracting, purifying and developing plant derived antioxidant compositions for use as cosmetics, dietary supplements/nutraceuticals, food additives or pharmaceuticals.

Phenolic compounds, including their subcategory, flavonoids, arena group of compounds that possess antioxidant properties, which are present in all plants and have been studied extensively in cereals, legumes, nuts, olive oil, vegetables, fruits, tea and red wine. There is considerable interest in these naturally occurring antioxidants and in methods of extracting these compounds from various plants and plant products. For example, U.S. Pat. No. 6,620,452 describes a process for extracting plant phenolics from a fruit or vegetable, and steps to provide a liquid or solid concentrate thereof. U.S. Pat. No. 5,932,623 describes a process for obtaining extracts from unripe fruits and purports to identify the polyphenol products that are present in the extract and U.S. Pat. No. 5,994,413 describes a mixture containing polyphenol products extracted from unripe fruits.

Antioxidants, including phenolics, have been identified in, and extracted from, various berries. For example, U.S. Pat. No. 6,676,978 describes a method for isolating a mixture of anthocyanins, bioflavonoids and phenolics from an edible berry using adsorbent resins. The use of compositions comprising these compounds to provide antioxidant and anti-inflammatory activities to a mammal is also described. U.S. Pat. No. 6,312,745 describes a process for dehydrating berries while maintaining their antioxidant compounds/activities. U.S. Patent Application No. 2003/0031734 is directed to blueberry extracts with anti-oxidant and anti-cancer properties and their use to inhibit tumour cell growth and oxidative activity in an animal.

Many plant derived antioxidants have been proposed for use as dietary supplements. For example, U.S. Patent Application No. 2002/0068102 describes a dietary supplement comprising natural juices and its use to reduce cellular damage by scavenging free radicals within the human body. The natural juices can be derived from, for example, natural grape concentrate, a natural blueberry juice concentrate and/or other natural juice concentrates. U.S. Patent Application No. 2003/0008048 describes a dietary nutritional supplement that may comprise blueberry, for helping the body resist the effects of the aging process and U.S. Patent Application No. 2003/003120 is directed to a phenolic fraction obtained from fruit and its use as a cosmetic, dietary, or nutraceutical preparation. Nutritional supplements are also described in U.S. Patent Application No. 2002168429. This patent application describes a method of producing reconstituted vegetable or fruit products that can then be used to prepare a dietary supplement. Fruit juices contemplated by this application include blueberry and cranberry juices, which are expressed from the berries and subsequently concentrated.

Fermentation can also be employed to modulate the antioxidant content of a plant derived products. For example, U.S. Pat. No. 5,498,412 describes a method for producing a natural antioxidant composition made from a plurality of fermented and milled materials of edible grains and pulses. In addition, wine fermentation has been reported to bring about multiple chemical modifications with respect to phenolic antioxidant profiles (Mazza, G., et al., (1999) *J. Agric. Food Chem.*, 47, 4009-4017; Talcott, S. T. & J. H. Lee (2002) *J. Agric. Food Chem.*, 50, 3186-3192).

Thus, the antioxidant content of fruits and vegetables varies considerably not only with species and growth conditions, but also with a number of other factors, including processing, fermentation, exposure to various temperatures, irradiation and pathogenic infection.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide an antioxidant producing bacterium and uses thereof. In accordance with an aspect of the present invention, there is provided a bacterial strain having all the identifying characteristics of the bacterium deposited under Accession Number 160103.

In accordance with another aspect of the present invention, there is provided a bacterial strain having a 16S rRNA gene comprising a nucleotide sequence that is at least about 97% identical to the sequence as set forth in SEQ ID NO:1.

In accordance with another aspect of the present invention, there is provided a process for producing an antioxidant-enriched fruit extract comprising: fermenting a fruit extract with a bacterial strain of the invention.

In accordance with another aspect of the present invention, there is provided a process for producing an antioxidant-enriched fruit extract, said method comprising: providing a sterile medium comprising a fruit extract, inoculating said sterile medium with a bacterial strain having all the identifying characteristics of the bacterium deposited under Accession Number 160103 to provide a bacterial culture; fermenting said bacterial culture to provide an antioxidant-enriched fruit extract, and recovering said antioxidant-enriched fruit extract.

In accordance with another aspect, there is provided an antioxidant-enriched fruit extract produced by a process of the invention.

In accordance with another aspect of the present invention, there is provided an antioxidant composition comprising a carrier or diluent and an antioxidant-enriched fruit extract produced by a process of the invention.

In accordance with another aspect, there is provided a use of an antioxidant-enriched fruit extract of the invention in the preparation of a cosmetic composition.

In accordance with another aspect, there is provided a use of an antioxidant-enriched fruit extract of the invention in the preparation of a pharmaceutical composition.

In accordance with another aspect, there is provided a use of an antioxidant-enriched fruit extract of the invention in the preparation of a nutraceutical, functional food, beverage or dietary supplement.

In accordance with another aspect, there is provided a use of an antioxidant-enriched fruit extract of the invention to deliver antioxidants to a mammal in need thereof.

In accordance with another aspect of the invention, there is provided a cosmetic composition produced by a process comprising the steps of: fermenting a fruit extract with a bacterial strain of the invention to provide an antioxidant-enriched fruit extract; and combining said antioxidant-enriched fruit extract with a cosmetically acceptable carrier or diluent.

In accordance with another aspect of the invention, there is provided a pharmaceutical composition produced by a process comprising the steps of: fermenting a fruit extract with a bacterial strain of the invention to provide an antioxidant-enriched fruit extract; and combining said antioxidant-enriched fruit extract with a pharmaceutically acceptable carrier or diluent.

In accordance with another aspect of the present invention, there is provided a cosmetic composition comprising an antioxidant-enriched fruit extract of the invention and a cosmetically acceptable carrier or diluent.

In accordance with another aspect of the present invention, there is provided a pharmaceutical composition comprising an antioxidant-enriched fruit extract of the invention and a pharmaceutically acceptable carrier or diluent.

In accordance with another aspect, there is provided a use of a pharmaceutical composition of the invention as an antioxidant in a mammal in need thereof.

In accordance with another aspect, there is provided a use of a pharmaceutical composition of the invention as an immunomodulator in a mammal in need thereof.

In accordance with another aspect, there is provided a use of a pharmaceutical composition of the invention to stimulate TNF-α production in a mammal in need thereof.

In accordance with another aspect, there is provided a use of α-bacterial strain of the invention in a fermentation process.

In accordance with another aspect, there is provided a use of a bacterial strain of the invention as a food additive.

In accordance with another aspect, there is provided a use of a bacterial strain of the invention to increase the antioxidant content of a food product.

In accordance with another aspect, there is provided a use of a bacterial strain of the invention to metabolise toxic phenolic compounds in a sample.

In accordance with another aspect, there is provided a composition comprising a bacterial strain of the invention and a suitable medium or stabiliser.

In accordance with another aspect, there is provided a kit comprising a bacterial strain of the invention and optionally one or more growth medium ingredient for propagation of the bacterial strain.

BRIEF DESCRIPTION OF THE FIGURES

FIG. 1 depicts a 1500 nucleotide sequence of the 16S rRNA gene of the bacterium deposited under with the International Depository Authority of Canada under Accession Number 160103 [SEQ ID NO: 1].

FIG. 6 depicts (A) the total phenolic content in GAE (mg of gallic acid equivalent/100 g of fresh weight) during fermentation of cranberry juice by the bacterium (Accession No. 160103) [Error bars indicate standard deviation for each day of fermentation.] and (B) the total phenolic content in GAE during fermentation of grape juice by the bacterium (Accession No. 160103).

FIG. 8 depicts the total phenolic content in GAE (mg of gallic acid equivalent/100 g of fresh weight) during fermentation of cranberry juice (A) by the bacterium (Accession No. 160103) under anaerobic conditions and (B) by a mixture of the bacterium (Accession No. 160103) and wine yeast. Error bars indicate standard deviation for each day of fermentation.

FIG. 10 depicts the inhibition of nitric oxide production (NO) from LPS/IFN-γ-activated macrophages by (A) cranberry juice, (B) blueberry juice and (C) phenolic compounds.

FIG. 11 depicts the relative inhibitory effect (%) of (A) cranberry juice, blueberry juice and phenolic compounds on nitric oxide production (NO) from LPS/IFN-γ-activated macrophages. Inhibitory effect achieved with (B) 125 μM GAE and (C) 250 μM GAE.

DETAILED DESCRIPTION OF THE INVENTION

Figure 2:
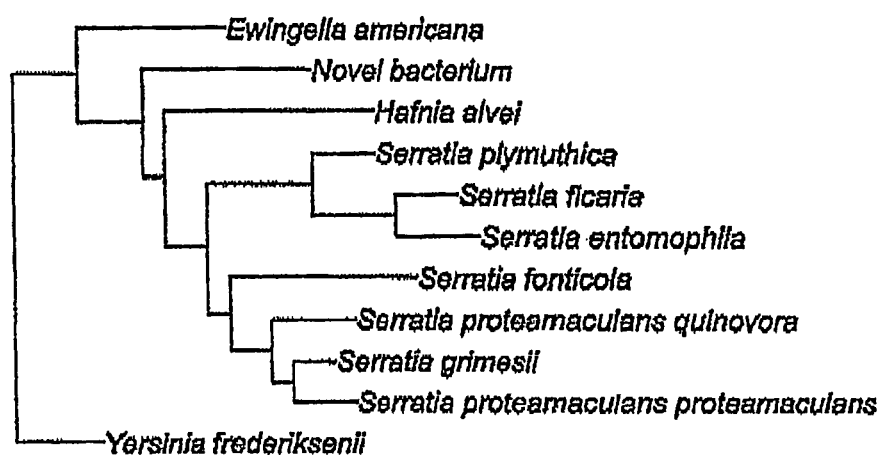
FIG. 2 depicts the phylogenetic analysis based on the partial 16S rRNA fragment for the bacterium (Accession No. 160103).

The present invention provides for a previously unidentified bacterial species that can be isolated from the microflora of lowbush blueberry (*Vaccinium angustifolium*) and which is capable of increasing the antioxidant content of its growth medium. The bacteria of the invention can be used, for example, to increase the antioxidant content of various foodstuffs, as a probiotic or as an additive to animal feed. The bacteria can also be used in fermentation processes to produce antioxidant-enriched fruit extracts, and in particular antioxidant-enriched berry extracts. The present invention thus further provides for antioxidant-enriched compositions produced by fermenting fruit extracts with a bacterium of the invention. Such compositions have application in the preparation of cosmetics, as dietary or nutritional supplements and food additives. The antioxidant-enriched compositions are also useful as therapeutics in the treatment of a disease, disorder or condition in a mammal associated with free radical damage or the formation of reactive oxygen species (ROS). The compositions of the invention have been demonstrated to have immunomodulatory properties and thus also have applications as therapeutics in the treatment of diseases and disorders related to the immune system.

DEFINITIONS

Unless defined otherwise, all technical and scientific terms used herein have the same meaning as commonly understood by one of ordinary skill in the art to which this invention pertains.

The term "sequence identity," as used herein, means that two polynucleotide sequences, a candidate sequence and a reference sequence, are identical (i.e. on a nucleotide-by-nucleotide basis) over the length of the candidate sequence. In comparing a candidate sequence to a reference sequence, the candidate sequence may comprise additions or deletions (i.e. gaps) of 20 percent or less as compared to the reference sequence (which does not comprise additions or deletions) for optimal alignment of the two sequences. Optimal alignment of sequences for determining sequence identity may be conducted using the local alignment algorithm of Smith and Waterman (*Adv. Appl. Math.* (1981) 2:482), the alignment algorithm of Needleman and Wunsch (*J. Mol. Biol.* (1970) 48:443), the search for similarity method of Pearson and Lipman (*Proc. Natl. Acad. Sci.* (*U.S.A.*) (1988) 85:2444), using computerised implementations of these algorithms (such as GAP, BESTFIT, FASTA, and TFASTA in the Wisconsin Genetics Software Package Release 7.0, Genetics Computer Group, 573 Science Dr., Madison, Wis.), using publicly available computer software such as ALIGN or Megalign (DNASTAR), or by inspection.

The term "percent (%) sequence identity," as used herein with respect to a reference sequence is defined as the percentage of nucleotide residues in a candidate sequence that are identical to the residues in the reference polynucleotide sequence after optimal alignment of the sequences and introducing gaps, if necessary, to achieve the maximum percent sequence identity.

The term "specifically hybridise," as used herein, refers to the ability of a nucleic acid sequence to bind detectably and specifically to a second nucleic acid sequence. A polynucleotide selectively hybridises to a target nucleic acid sequence under hybridisation and wash conditions that minimise appreciable amounts of detectable binding to non-specific nucleic acid sequences. High stringency conditions can be used to achieve specific hybridisation conditions as known in the art. Typically, hybridisation and washing conditions are performed at high stringency according to conventional hybridisation procedures. Washing conditions are typically 1-3×SSC, 0.1-1% SDS, 50-70° C. with a change of wash solution after about 5-30 minutes.

The term "fruit extracts," as used herein, refers to a preparation derived from a fruit or one or more part thereof, including juice, peel, rind, pith, pips and flesh. The preparation can be derived from the fruit or fruit part by a variety of techniques, including for example, maceration, squeezing, pressing, expressing, distillation, steeping, soaking, infusion, filtration or concentration of the fruit or fruit part. Combinations of these techniques can also be used.

"Substantially pure' or "isolated," as used herein with reference to a compound found in a fruit extract, indicates that the compound is the predominant species present in a composition (i.e. on a molar basis it is more abundant than any other individual compound in the composition). Typically, substantially pure that the compound constitutes at least about 20% of all macromolecular species present in the composition. In one embodiment, a substantially pure compound refers to a compound that constitutes more than about 30% of all macromolecular species present in a composition. In another embodiment, a substantially pure compound refers to a compound that constitutes more than about 40% of all macromolecular species present in a composition. In other embodiments, a substantially pure compound refers to a compound that constitutes more than about 50%, more than about 60% and more than about 70% of all macromolecular species present in a composition.

As used herein, the term "about" refers to a +/−10% variation from the nominal value. It is to be understood that such a variation is always included in any given value provided herein, whether or not it is specifically referred to.

Bacteria of the Present Invention

A representative bacterium of the present invention, *Serratia vaccinii*, was isolated from the microflora of lowbush blueberry (*Vaccinium angustifolium*) and deposited with the International Depository Authority of Canada (IDAC), Bureau of Microbiology, Health Canada, 1015 Arlington Street, Winnipeg, Manitoba, Canada on Jan. 16, 2003 under Accession Number 160103. Analysis of the biochemical profile and partial sequence of the 16S rRNA gene of the bacterium as described herein indicates that it belongs to the family Enterobacteriaceae.

The bacterium deposited under Accession Number 160103 is characterised in that it is a gram negative, catalase positive, facultatively anaerobic coccobacillus. The bacterium has a fermentative metabolism and can ferment a number of sugars, including D-glucose, D-fructose, D-mannose, arbutin, esculin, salicin, saccharose and D-raffinose. Under certain conditions, the bacterium can also ferment mannitol, lactose and trehalose as described herein in Example I. The bacterium produces acetoin, hydrolyses hippurate and produces a number of enzymes including, pyrrolidonyl arylamidase, α-galactosidase, β-galactosidase, alkaline phosphatase and leucine arylamidase.

The bacterium deposited under Accession Number 160103 can further be characterised as having a 16S rRNA gene sequence that comprises the nucleotide sequence as set forth in SEQ ID NO:1.

As is known in the art, bacterial species are often represented by a number of different strains that share the same characteristics. The present invention, therefore, encompasses strain variants of the bacterium deposited under Accession Number 160103. In accordance with the present invention, these strains possess the same biochemical characteristics as outlined above for the bacterium deposited under Accession Number 160103.

The biochemical characteristics of the bacteria encompassed by the present invention can readily be determined using standard techniques known in the art. For example, the bacterium can be identified as gram-negative by the fact it does not retain crystal violet stain in the presence of alcohol or acetone. The fermentative abilities of the bacterium can be determined, for example, by using one of a variety of kits available commercially for this purpose (for example, the API and VITEK kits from BioMérieux, Marcy-l'Éttoile, France).

As indicated above, the bacterium deposited under Accession Number 160103 has a 16S rRNA gene sequence that comprises the nucleotide sequence as set forth in SEQ ID NO:1. It is well known in the art, however, that bacteria of the same species need not share 100% sequence identity in their 16S rRNA gene sequences and it is generally accepted that a 3% variation between the 16S rRNA gene sequences of two bacteria is the point at which two strains may be considered to be separate species (see, for example, Vandamme, et al., (1996) *Microbiol. Reviews* 60:407-48; Kolbert & Persing, (1999) *Curr. Microbiol.*, 2:299-305). Thus, a species is defined by at least 97% sequence identity in the 16S rRNA gene sequence. Bacteria considered to be within the scope of the present invention, therefore, are characterised in that their 16S rRNA gene comprises a sequence that is at least 97% identical to the sequence as set forth in SEQ ID NO:1. In one embodiment, the bacteria are characterised in that their 16S rRNA gene comprises a sequence that is at least 97.5% identical to the sequence as set forth in SEQ ID NO:1. In another embodiment, the bacteria are characterised in that their 16S rRNA gene comprises a sequence that is at least 98% identical to the sequence as set forth in SEQ ID NO:1. In a further embodiment, the bacteria are characterised in that their 16S rRNA gene comprises a sequence that is at least 98.2% identical to the sequence as set forth in SEQ ID NO:1. In still another embodiment, the bacteria are characterised in that their 16S rRNA gene comprises a sequence that is at least 98.5% identical to the sequence as set forth in SEQ ID NO:1. In other embodiments, the bacteria are characterised in that their 16S rRNA gene comprises a sequence that is at least 98.8%, at least 99% and at least 99.5% identical to the sequence as set forth in SEQ ID NO:1.

In an alternate embodiment, the bacteria are characterised in that the sequence of the 16S rRNA gene comprises at least 100 consecutive nucleotides of the sequence as set forth in SEQ ID NO:1, for example, at least 250 consecutive nucleotides of the sequence as set forth in SEQ ID NO:1. In other embodiments, the 16S rRNA gene of the bacteria comprises at least 500, 750 or 1000 consecutive nucleotides of the sequence as set forth in SEQ ID NO:1.

Sequencing of the 16S rRNA gene of the bacterium of interest can be readily conducted using DNA isolation and sequencing techniques known in the art [see, for example, Ausubel et al., *Current Protocols in Molecular Biology*, J. Wiley & Sons, NY] or using commercially available kits such as the MicroSeq™ 16S rRNA Gene Kit and software, available from Applied Biosystems. Comparison of the identified sequence with that set forth in SEQ ID NO:1 can be conducted using standard techniques including, for example, the use of publicly available software, such as BLAST (available from the NCBI website) and CLUSTALW (available from the EMBL-EBI website).

The present invention thus also provides for methods of identifying bacterial strains of the same species as the bacterium deposited under Accession Number 160103, which are capable of increasing the phenolic antioxidant content of a growth medium. The methods employ nucleic acid probes comprising the sequence set forth in SEQ ID NO:1, or a fragment thereof, to screen DNA derived from other bacterial strains to identify those whose 16S rRNA gene DNA specifically hybridises to the nucleic acid probe. Methods of screening bacterial DNA samples for sequences that hybridise to a known probe are standard in the art [see, for example, Ausubel et al., *Current Protocols in Molecular Biology*, J. Wiley & Sons, NY]. Bacteria that are identified as having DNA sequences that specifically hybridise to the probe can then be analysed further by sequence analysis.

If necessary, PCR primers can be designed based on the sequence set forth in SEQ ID NO:1 that would allow amplification of target DNA from the bacterium under investigation in order to facilitate hybridisation screening and/or sequence analysis. Design of appropriate primers from the sequence set forth in SEQ ID NO:1 is considered to be within the ordinary skills of a worker in the art. Alternatively, primers designed to amplify the hypervariable portion of the 16S rRNA gene can be based on the sequences that flank this portion of the gene ad which are conserved in most Eubacteria. Kits for the isolation and sequencing of bacterial 16S rRNA genes are commercially available (for example, the MicroSeq® Microbial Identification System from Applied Biosystems, Foster City, Calif.). Bacteria having a 16S rRNA gene sequence that comprises a sequence at least 97% identical to SEQ ID NO:1 are selected and their biochemical profiles are assessed for similarity to that of the bacterium deposited under Accession No. 160103.

Alternatively, the methods of identifying the bacteria of the invention can comprise first isolating a bacterium from lowbush blueberries and subsequently determining the biochemical profile of the isolated bacterium as described above. Bacteria having a biochemical profile that matches that of the bacterium deposited under Accession No. 160103 are selected. Analysis of the 16S rRNA gene sequence is then conducted and those bacteria having a 16S rRNA gene sequence that comprises a sequence at least 97% identical to the sequence as set forth in SEQ ID NO:1 are selected as bacteria of the invention.

Bacterial strains selected by the above methods can be further tested for their ability to increase the antioxidant content of a growth medium using techniques known in the art such as those described herein.

Isolation and Propagation

The bacteria of the present invention can be isolated from lowbush blueberry microflora by the methods described herein.

For example, in one embodiment of the present invention, the bacterium is isolated from the surface of lowbush blueberries by inoculation of a tryptic soy broth with whole lowbush blueberry fruits, followed by growth at 25° C. for 36 hrs, and subsequent selection on tryptic soy agar by serial dilution. Each bacterial isolate can then be tested for antioxidant production during fermentation, for other biochemical properties as described above, or by sequence analysis in order to determine whether it is a bacterium of the invention.

The bacteria of the invention can be maintained and propagated on a variety of different media using standard culture techniques. Examples of suitable media include; but are not limited to, tryptic soy broth or agar, Simmons citrate agar, MRS agar, Voges-Proskauer agar and potato dextrose agar. In one embodiment of the present invention, the bacterium is maintained and/or propagated on tryptic soy broth or agar.

For propagation, the bacteria of the invention can be grown at a temperature between about 8° C. and about 36° C., however, the growth rate at temperatures between 10° C. and 8° C. is typically diminished compared to that at higher temperatures. In one embodiment of the invention, therefore, the bacteria are propagated between about 10° C. and about 36° C. In another embodiment, the bacteria are propagated between about 20° C. and about 25° C.

Genetic Engineering

The present invention further contemplates genetic engineering of the bacterium in order to improve certain desirable traits and/or to decrease or eliminate less desirable traits. For example, the bacterium could be engineered to enhance the production of antioxidant compounds. Methods of genetically engineering bacteria are well known in the art.

Antioxidant-Enriched Compositions

The present invention further provides for antioxidant-enriched compositions comprising fruit extracts that have been fermented with a bacterium of the invention to enrich their antioxidant content. In one embodiment of the invention, the fermented fruit extract is enriched in phenolic antioxidants.

The fermented fruit extracts can be partially or substantially purified if desired using standard techniques in order to concentrate the antioxidant components further or to isolate one or more antioxidant compounds therefrom. Thus, the compositions can comprise fermented fruit extracts that have not undergone further processing, or they can comprise concentrates or solids derived from the fermented fruit extracts, partially purified fermented fruit extracts, or partially or substantially purified compounds derived from the fermented fruit extracts.

Production of Fermented Fruit Extracts

The present invention provides for a process of bacterial fermentation to provide antioxidant-enriched Suit extracts.

To produce antioxidant-enriched fruit extracts by fermentation with a bacterium of the invention, an appropriate medium is first selected. Typically, the medium contains at least 10% fruit extract together with sufficient amounts and proportions of ions to support bacterial growth. To maximise the amount of antioxidants produced by the fermentation process, higher proportions of fruit extracts can be incorporated into the growth medium. For example, media containing at least 20% fruit extract, at least 30% fruit extract, at least 40% fruit extract, at least 50% fruit extract, at least 60% fruit extract and at least 70% fruit extract can be used. One skilled in the art will understand that media may be formulated that contain up to 100% fruit extract provided that sufficient amounts and proportions of ions are incorporated to support bacterial growth. One example of an appropriate medium is a blended medium containing about 50% fruit and about 50% minimal media (i.e. water containing sufficient amounts and proportions of ions to support bacterial growth).

The pH of the medium is adjusted to between about 5.0 and about 3.3 using standard techniques, in order to support the growth of the bacterium.

Fermentation of a medium containing grape or berry extracts by the bacterium deposited under Accession No. 160103 has been shown to result in an increase in the total amount of antioxidants in the medium. It is contemplated, however, that the medium can be prepared using extracts derived from one, or a mixture, of a variety of fruits. For example, the medium can be prepared from grapes or from berries including, but not limited to, blueberries, cranberries, lingonberries, blackcurrants, chokecherries, chokeberries, raspberries, blackberries, elderberries and Saskatoon berries, or various combinations thereof. In one embodiment of the present invention, the fruit used in the medium is one or more of: grapes, blueberries, cranberries, elderberries, chokecherries, blackcurrants, and Saskatoon berries. In another embodiment of the present invention, the fruit used in the medium is one or more berry from the genus *Vaccinium* (including blueberries, cranberries and lingonberries). The amount of antioxidant-enrichment that is achieved from the fermentation will vary depending on the fruit selected and can be determined using standard procedures such as those described herein and in the literature.

As is known in the art, many commercially grown fruits are treated with chemicals to prevent the growth of microbial contaminants, which could interfere with the ability of the bacteria of the invention to ferment media comprising these treated fruits. Thus, in one embodiment of the invention, the fruit utilised in the preparation if the medium is organic. In another embodiment, the fruit is a wild fruit.

The medium can be readily prepared, for example, by blending an appropriate amount of one or more fruit with water or a minimal medium and sterilising the resultant solution. When water is used, salts and ions can be added as required. If desired, other components that promote the growth of the bacterium, such as amino acids or carbohydrates, can be incorporated into the medium.

The one or more fruit used to prepare the medium can be fresh, frozen, tinned or dried and can be a whole fruit, or a pulp, paste, puree, juice, juice concentrate or solid or a fruit nectar. Alternatively, a powdered form of the fruit can be used, in which case it can be reconstituted in water or directly in minimal medium. "Pulp" and "puree" refer to both heat-treated and non heat-treated whole fruit pieces, which have been mechanically transformed into soft mixture or suspension, whereas a "paste" refers to a pulp or puree that has been partially dehydrated.

The pH of the medium can also be adjusted as necessary such that the starting pH of the medium is above 3.2. As indicated above, a suitable pH for the medium is in the range from about 5.0 and about 3.3. In one embodiment of the present invention, the starting pH is about 3.7 to about 5.0. In other embodiments, the starting pH is between about 4.0 and about 5.0 and between about 4.5 and about 5.0.

The suspension can be filtered or centrifuged to remove particulate matter prior to sterilisation, if required. If it is required that the medium has a certain phenolic content prior to fermentation, the medium is sterilised by filtration rather than by heat, as excessive heat can degrade the phenolic compounds. In one embodiment of the present invention, the medium is prepared by blending fresh berries with an equal volume of Minimal Broth Davis without dextrose, centrifuging the medium to remove particulate matter and sterilising by filtration through an appropriate filter.

Fermentation is initiated by inoculation of the medium with an appropriate number of bacterial cells. The inoculant can be in the form of a fraction of a starter culture, as a swab comprising cells taken from a culture of the bacteria on a solid phase, such as agar, or as a fraction of or swab form a frozen culture of the bacteria. When a starter culture is used, the starter culture can employ the same or a different medium, such as one of those described above for propagation of the bacteria.

Methods of fermentation are well-known in the art. In accordance with the present invention, once the medium has been inoculated with the bacterium, the culture is fermented at a temperature between about 8° C. and about 36° C. In one embodiment, the bacterium is fermented at a temperature between about 10° C. and about 30° C. In other embodiments, the bacterium is fermented at a temperature between about 15° C. and about 25° C. and between about 20° C. and about 24° C.

As the bacterium is facultatively anaerobic, the fermentation can take place under aerobic or anaerobic conditions. In one embodiment, the fermentation is conducted under aerobic conditions. In another embodiment, it is conducted under anaerobic conditions.

Typically the fermentation is allowed to proceed for between about 1 day and about 12 days. Maximal amounts of phenolic antioxidants are usually obtained after about 2 to about 5 days of fermentation under aerobic conditions and after about 8 days of fermentation under anaerobic conditions. In one embodiment, therefore, the fermentation proceeds for about 1 day to about 10 days. In another embodiment, the fermentation proceeds for about 1 day to about 7 days. In other embodiments, the fermentation proceeds for about 2 days to about 5 days, for about for about 3 days to about 4 days and for about 4 days to about 10 days.

In some instances, the pH of the medium may vary during fermentation and this variation can affect the antioxidant content. Thus, when applicable, the pH of the medium can be monitored and adjusted as necessary during the fermentation using standard techniques.

Assessing the Antioxidant Content of the Fermented Fruit Extracts

After fermentation with the bacterium, the antioxidant content of the fermented medium can be determined using standard analytical methods known in the art. Anthocyanin content can be measured, for example, by spectrophotometric methods such as those described by Fuleki and Francis (*J. Food Sci.* (1968) 33:73-83). Total phenolic content can be assessed, for example, by the Folin-Ciocalteau method (see, for example, Velioglu et al., (1998) *J. Agric. Food Chem.* 46:4113-4117) or by chromatography techniques, such as high performance liquid chromatography (HPLC).

In accordance with one embodiment of the present invention, the phenolic antioxidant content of the fermented medium is increased by at least 1.5-fold after a 4-day fermentation under aerobic conditions when compared to unfermented medium. In another embodiment, the phenolic antioxidant content of the fermented medium is increased by at least 1.75-fold after a 4-day fermentation with compared to unfermented medium. In a further embodiment, the phenolic antioxidant content of the fermented medium is increased by at least 2-fold after a 4-day fermentation with compared to unfermented medium.

In an alternate embodiment, the phenolic antioxidant content of the fermented medium is increased by at least 1.5-fold after an 8-day fermentation under aerobic conditions when compared to unfermented medium.

Further Processing and/or Purification of the Fermented Fruit Extracts

In accordance with the present invention, the fermented fruit extracts produced by the above-described process can be further processed or purified for preparation of the antioxidant-enriched compositions. Thus, for example, the fermented fruit extracts can be further reduced to provide a solid or liquid concentrate thereof using standard methods known in the art. Alternatively, compounds having antioxidant properties can be concentrated in, or isolated from, the fermented fruit extracts by standard chemical techniques, for example, by extraction techniques, filtration techniques, chromatographic techniques, such as HPLC, or electrophoretic techniques, such as capillary electrophoresis.

"Purifying" a fermented fruit extract in the context of the present invention indicates that the extract undergoes substantial or partial purification, and/or fractionation using one or more of a number of techniques well known in the art, for example, solid-liquid extraction, liquid-liquid extraction, solid-phase extraction (SPE), membrane filtration, ultrafiltration, dialysis, electrophoresis, solvent concentration, centrifugation, ultracentrifugation, liquid or gas phase chromatography (such as size exclusion, affinity, and the like) with or without high pressure, lyophilisation, evaporation, precipitation with various "carriers" (such as PVPP, carbon, and the like). One skilled in the art, would appreciate how to use such techniques, in a sequential fashion, in order to enrich each successive fraction in the activity of interest (i.e. antioxidant capacity) by following its activity throughout the purification procedure.

Solid-liquid extraction means include the use of various solvents including supercritical solvents and extractors such as soxhlet extractors, vortex shakers, ultrasounds and the like to enhance extraction, as well as recovery by filtration, centrifugation and related methods as described in the literature (see, for example, R. J. P. Cannell, *Natural Products Isolation*, Humana Press, 1998). Examples of solvents that may be used include, but are not limited to, hydrocarbon solvents, chlorinated solvents, organic esters, organic ethers, alcohols, water, and mixtures thereof. In the case of supercritical fluid extraction, the invention also covers the use of modifiers such as those described in V. H. Bright (*Supercritical Fluid Technology*, ACS Symp. Set. Vol. 488, ch. 22, 1999).

Liquid-liquid extraction means include the use of various mixtures of solvents known in the art, including solvents under supercritical conditions. Typical solvents include those listed above. The liquid-liquid extraction can be effected manually, or it can be semi-automated or completely automated, and the solvent can be removed or concentrated by standard techniques in the art (see, for example, S. Ahuja, *Handbook of Bioseparations*, Academic Press, 2000).

Solid-phase extraction (SPE) techniques include the use of cartridges, columns or other devices known in the art. The sorbents that may be used with such techniques include, but are not limited to, silica gel (normal phase), reverse-phase silica gel (modified silica gel), ion-exchange resins, and fluorisil. The invention also includes the use of scavenger resins or other trapping reagents attached to solid supports derived from organic or inorganic macromolecular materials to remove selectively active ingredients or other constituents from the extracts.

Membrane, reverse osmosis and ultrafiltration means include the use of various types of membranes known in the art, as well as the use of pressure, vacuum, centrifugal force, and/or other means that can be utilised in membrane and ultrafiltration processes (see, for example, S. Ahuja, *Handbook of Bioseparations*, Academic Press, 2000).

Dialysis means include membranes having a molecular weight cut-off varying from less than about 0.5 KDa to greater than about 50 KDa. The invention also covers the recovery of purified and/or fractionated extracts from either the dialysate or the retentate by various means known in the art including, but not limited to, evaporation, reduced pressure evaporation, distillation, vacuum distillation, and lyophilization.

Various chromatographic means are known in the art and described in the literature (see, for example, G. Sofer, L. Hagel, *Handbook of Process Chromatography*, Academic Press, 1997) and are suitable for use in the present invention. Examples include, but are not limited to, regular column chromatography, flash chromatography, high performance liquid chromatography (HPLC), medium pressure liquid chromatography (MPLC), supercritical fluid chromatography (SFC), countercurrent chromatography (CCC), moving bed chromatography, simulated moving bed chromatography, expanded bed chromatography, one- and two dimension thin-layer chromatography (1D- and 2D-TLC), high performance thin-layer chromatography (HPTLC), and centrifugal thin-layer chromatography (centrifugal TLC). With each chromatographic method, examples of sorbents that may be used include, but are not limited to, silica gel, alumina, fluorisil, cellulose and modified cellulose, various modified silica gels, ion-exchange resins, size exclusion gels and other sorbents known in the art (see, for example, T. Hanai, *HPLC: A Practical Guide*, RSC Press, UK 1999).

Selective precipitation means includes the use of various solvents and solvent combinations, the use of temperature changes, the addition of precipitant and/or modifiers, and/or modification of the pH by addition of base or acid to effect a selective precipitation of active ingredients or other constituents.

The invention also includes the fractionation, partial purification, and/or purification of active ingredients and extracts by steam distillation, hydrodistillation, or other related methods of distillation known in the art (see, for example, L. M. Harwood, C. J. Moody, *Experimental Organic Chemistry*, Blackwell Scientific Publications, UK, 1989).

The process of purifying the fermented fruit extracts or compounds derived therefrom also includes the concentration of the extracts by solvent removal from the original extract, fractionated extract, or purified extract. Techniques for solvent removal are known to those skilled in the art and include, but are not limited to, rotary evaporation, distillation (normal and reduced pressure), centrifugal vacuum evaporation (speed-vac), and lyophilization.

Testing the Fermented Fruit Extracts

The fermented fruit extracts can be tested for their antioxidant capacity and/or their immunomodulatory properties using standard techniques known in the art. Exemplary protocols are provided herein.

1. Antioxidant Capacity

The antioxidant capacity of the fermented fruit extracts can be tested using a number of standard methods known in the art. For example, antioxidant capacity can be determined by assessment of the radical scavenging ability, using such techniques as the DPPH (2,2-diphenyl-1-picrylhydrazyl) method, which is described herein. Other suitable methods include, but are not limited to, the TEAC (trolox equivalent antioxidant capacity) and ORAC (oxygen radical absorbance capacity) methods.

The TEAC assay measures the ability of a test extract to prevent or quench free radicals formation. This assay employs 2,2'-azinobis-(3-ethylbenzothiazoline-6-sulfonic acid) (ABTS), which reacts with hydrogen peroxide in the presence of a peroxidase enzyme to form radical cations. The presence of the radical cations can be detected optically through their effect on 6-hydroxy-2,5,7,8-tetramethylchroman-2-carboxylic acid (trolox). Inhibition of this free radical formation by a test extract is measured and provides an indication of the antioxidant capacity of the extract.

The ORAC assay uses 2'-azobis-(2'-amidinopropane)-dihydrochloride (AAPH) to generate peroxyl radicals. The radicals are optically measured as the fluorescence quenching and/or destruction of the algal pigment β-phycoerythrin. The assay can be automated by using instruments capable of fluorescence lifetime or total fluorescence measurements, thus allowing the free-radical quenching power of test extracts to be analysed.

A number of other standard assays to determine the ability of the fermented fruit extracts to trap free radicals can be used in order to provide an indication of the antioxidant capacity of the extracts. For example, the total (peroxyl) radical-trapping antioxidant potential (TRAP) assay can be employed. In this assay a lipid sample is contacted with AAPH in the presence of a test extract. AAPH initiates formation of peroxyl radicals and an oxygen electrode is used to measure the rate that the sample resists peroxidation (for example, by measuring the rate of oxygen uptake). This method is generally most effective for measuring the antioxidant capacity of lipid soluble extracts.

Another example of a suitable assay is the total oxyradical scavaging species (TOSC) assay, which quantifies the reactive oxygen species scavaging potential of a test extract. The assay utilises thermal decomposition of ABAP to generate peroxy radicals, which in turn generate ethylene gas by oxidatively decomposing α-keto-γ-methiobutyric acid. Test extracts that scavenge the reactive oxygen can prevent or diminish the formation of ethylene, which can be measured by a gas chromatograph. Electron spin resonance (ESR) spectrophotometric assays based on Fremy's salt and galvinoxyl radical scavenging can also be used (see, for example, Schwartz, et al., (2001) *Eur. Food Res. Technol.* 212:319-328).

2. Immunomodulatory Properties

The immunomodulatory properties of the fermented fruit extracts can be tested using standard methods known in the art. For example, the ability of the extracts to activate or inhibit cytokine release or nitric oxide production in macrophages can be studied in vitro using a suitable monocyte/macrophage cell line, such as those available from the American Type Culture Collection (ATCC) and various commercial sources (for example, RAW 264.7 and derivatives). Alternatively, monocytes/macrophages can be obtained from mammalian blood samples using standard isolation procedures.

Cultures of monocytes/macrophages can be conducted with various amounts of the fermented fruit extracts and incubated for a suitable length of time. The cells can be stimulated with LPS and/or IFN-γ as necessary. Stimulation can be conducted prior to, at the same time as or after contact with the test extract. The level of one or more cytokine (such as TNF-α, IL-1, IL-1α, IL-2, IL-4, IL-6, IL-8, GM-CSF) in the cell supernatants after treatment can be measured, for example, using various commercially available ELISA kits. Nitric oxide production can be determined using methods based on the Griess reaction for measuring nitrite concentration.

In accordance with one embodiment of the present invention, the fermented fruit extracts are capable of inhibiting monocyte/macrophage nitric oxide production. In another embodiment, the fermented fruit extracts are capable of stimulating TNF-α release from monocytes and/or macrophages.

The fermented fruit extracts can also be tested for cytotoxicity using standard techniques. For example, the extracts can be assayed for their ability to inhibit cell growth in vitro. In general, cells of a specific test cell line are grown to an appropriate density (e.g. approximately $1 \times 10^4$) and the test extract is added. After an appropriate incubation time (for example 48 to 74 hours), cell density is assessed. Methods of measuring cell density are known in the art, for example, cell density can be assessed under a light-inverted microscope by measuring the surface of the culture plate covered by the cell monolayer; or by using the resazurin reduction test (see Fields & Lancaster (1993) *Am. Biotechnol. Lab.* 11:48-50; O'Brien et al., (2000) *Eur. J. Biochem.* 267:5421-5426 and U.S. Pat. No. 5,501,959), the microculture tetrazolium (MTT) assay (Alley, M C et al, *Cancer Research* 48:589-601, 1988), the sulforhodamine assay (Rubinstein et al., (1990) *J. Natl. Cancer Inst.* 82:113-118) or the neutral red dye test (Kitano et al., (1991) *Euro. J. Clin. Investg.* 21:53-58; West et al., (1992) *J. Investigative Derm.* 99:95-100).

The fermented fruit extracts can further be tested for their immunomodulatory properties in vivo using suitable murine models. For example, a mouse xenograft model using an appropriate cancer cell line can be used to assess the ability of the extracts to modulate cytokine production, macrophage infiltration into the tumour, apoptosis and/or tumour growth. Cytokine production and macrophage infiltration can be measured by assessing the presence or absence of appropriate cellular markers using histochemical or immunohistochemical techniques as is known in the art. Apoptosis can be measured, for example, using TUNEL staining. Tumour cell growth can be assessed by measurement of the tumour size or weight over a suitable test period. These and other standard methods for determining immunomodulatory effects of test compounds are known in the art (see, for example, Enna, et al., *Current Protocols in Pharmacology*, J. Wiley & Sons, Inc., New York, N.Y.).

Uses
Bacteria

The bacteria of the present invention can be used as food additives or probiotics in order to increase the antioxidant content of foods or the bioavailability of antioxidants in the gastro-intestinal tract; For example, the bacteria may be added to foods, such as yoghurt, cottage cheese, fruit, legume or other vegetable juice and fruit based snacks. Alternatively, the bacteria can be lyophilised and provided in tablet form as a dietary supplement. The bacteria can also be added to animal feed in order to improve its antioxidant content.

The present invention, therefore, also provides for a process of increasing the antioxidant content of a food or beverage product comprising fermenting the bacteria with one or more ingredient during the production of a food or beverage product.

As demonstrated herein, the bacteria of the invention are compatible with the yeast *Saccharomyces cerevisae*, which is used in the production of foods, such as breads and baked products, and fermented beverages, such as wine. Wine is known to be is a good source of antioxidants and fermentation using *Saccharomyces cerevisae* in conjunction with the bacteria of the invention can be used to increase the total amount of antioxidants present in the final product. In one embodiment of the present invention, therefore, the bacterium is added to a wine during fermentation to increase the antioxidant content thereof. In another embodiment, the bacterium is used to increase the antioxidant content of a bread or baked product.

The bacteria may also have utility in the field of decontamination, wherein the bacteria could be used to metabolise toxic phenolic compounds in a contaminated sample.

Antioxidant-Enriched Compositions

The antioxidant-enriched compositions comprising fermented fruit extracts have a variety of applications. For example, the composition can readily be incorporated into nutritional formulations, such as nutraceuticals, functional food and beverage products and dietary supplements as a source of antioxidants. The present invention contemplates that the composition can be added directly to a food or beverage product or that it can be tabletted for consumption as a supplement. For example, the composition can be incorporated into a fruit-based product such as a fruit bar, fruit-flavoured confectionery, jam, jelly, fruit flavoured beverage, and the like. Tabletted supplements can be provided in the form of tablets, caplets, hard or soft gelatine capsules, and the like.

The antioxidant-enriched compositions of the invention are also suitable for use in cosmetic formulations, for example, in skin and hair care formulations, including those formulated to help reduce stress-related effects, in skin rejuvenating formulations, including those formulated to help reduce wrinkles and/or aging marks, and in cosmetic formulations intended to help prevent skin damage by UV radiation.

For cosmetic applications, the compositions can be provided as a cosmetically suitable formulation, such as a lotion, gel, cream, liquid cream, ointment, oil base, or as a sprayable liquid form. Such formulations can include a cosmetically acceptable vehicle to act as a diluent, dispersant or carrier for the composition, so as to facilitate their distribution when the formulation is applied to the skin. Cosmetically acceptable vehicles other than water can include liquid or solid emollients, solvents, humectants, thickeners and powders. Various types of skin benefit ingredients can also be optionally included in the cosmetic formulations. Examples of skin benefit ingredients include, but are not limited to, sunscreens, essentially fatty acids, antioxidants, retinoids and tanning agents. The cosmetic formulations can be packaged in a suitable container to suit the viscosity and intended use. For example, a lotion or fluid cream can be packaged in a bottle or a roll-ball applicator, a capsule, a propellant-driven aerosol device or a container fitted with a pump suitable for finger operation. When the composition is a cream, it can simply be stored in a non-deformable bottle or squeeze container, such as a tube or a lidded jar.

It is further contemplated that the compositions can be used as additives for the preservation of various foodstuffs, as stabilisers in personal care formulations, as preservatives in packaging for foodstuffs, such as cereal boxes and the like, and as preservatives against oxidative degradation of plastics.

Pharmaceutical Applications

The present invention provides for the use of the antioxidant-enriched compositions to treat, ameliorate or prevent a disease, disorder or condition in a mammal associated with free radical damage or the formation of reactive oxygen species (ROS). Examples of such diseases, disorders or conditions include cancer, diabetes mellitus, neurodegenerative diseases (such as multiple sclerosis, Parkinson's disease, Alzheimer's disease, dementia), arthritis, atherosclerosis, coronary heart diseases, cataracts, cognitive dysfunction, skin photo aging, skin wrinkles, sunburn, melanoma, and degenerative processes associated with aging.

The present invention further provides for the use of the compositions as immunomodulators for the treatment of a disease or disorder involving the immune system in a mammal. The ability of the compositions to stimulate TNF release also renders them useful in the treatment of infectious diseases, cancer and endometriosis.

When used therapeutically, the compositions of the invention can be used primarily as a pharmaceutical or drug, or they may be used in the context of complementary medicine where the aim is the supplement the effects of, or decrease the side effects associated with, conventional medicine. Thus, the compositions can be used as an adjuvant to conventional drugs, or they can be used to help decrease the side effects associated with the drugs, for example, with cancer chemotherapeutics.

For pharmaceutical applications, the compositions are formulated as pharmaceutically acceptable compositions by admixture with a physiologically acceptable carrier, excipient, binder or diluent.

The pharmaceutical compositions according to the invention can be in solid, semisolid or liquid from and can be adapted for oral, parenteral, rectal, inhalation, or topical administration, and can be provided in unit dosage form. The pharmaceutical composition may be adapted for slow release in vivo as known in the art. The pharmaceutical compositions may be used in conventional form including, but not limited to, solutions, syrups, troches, lozenges, aqueous or oily suspensions, dispersible powders or granules, emulsions, hard or soft capsules, elixirs, injectables, tablets, capsules, suppositories, hydrophobic and hydrophilic creams and lotions. The term parenteral as used herein includes subcutaneous injections, intravenous, intrathecal, intramuscular, intrasternal injection or infusion techniques. Other drugs may be included in the pharmaceutical composition if desired.

Pharmaceutical compositions intended for oral use may be prepared according to methods known in the art and may contain one or more agents such as sweetening agents, flavouring agents, colouring agents and preserving agents in order to provide pharmaceutically elegant and palatable preparations. Tablets contain the antioxidant-enriched compositions in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate: granulating and disintegrating agents for example, corn starch, or alginic acid: binding agents, for example starch, gelatine or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Pharmaceutical compositions for oral use may also be presented as hard gelatine capsules wherein the antioxidant-enriched composition is mixed with an inert solid diluent, for example, calcium carbonate, calcium phosphate or kaolin, or as soft gelatine capsules wherein the active ingredient is mixed with water or an oil medium, for example peanut oil, liquid paraffin or olive oil.

Aqueous suspensions contain antioxidant-enriched compositions in admixture with excipients suitable for the manufacture of aqueous suspensions. Such excipients are suspending agents, for example, sodium carboxymethylcellulose, methyl cellulose, hydropropylmethylcellulose, sodium alginate, polyvinylpyrrolidone, gum tragacanth and gum acacia: dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example hepta-deca-ethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxy-benzoate, one or more colouring agents, one or more flavouring agents or one or more sweetening agents, such as sucrose or saccharin.

Oily suspensions may be formulated by suspending the antioxidant-enriched compositions in a vegetable oil, for example, arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide palatable oral preparations.

Dispersible powders and granules suitable for preparation of an aqueous suspension by the addition of water provide the antioxidant-enriched compositions in admixture with a dispersing or wetting agent, suspending agent and one or more preservatives. Suitable dispersing or wetting agents and suspending agents are exemplified by those described above. Additional excipients, for example, sweetening, flavouring and colouring agents, may also be present.

Pharmaceutical compositions may also be in the form of oil-in-water emulsions. The oil phase may be a vegetable oil, for example, olive oil or arachis oil, or a mineral oil, for example liquid paraffin or mixtures of these. Suitable emulsifying agents may be naturally-occurring gums, for example, gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monoleate. The emulsions may also contain-sweetening and flavouring agents.

Syrups and elixirs may be formulated with sweetening agents, for example, glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulation according to methods known in the art using suitable dispersing or wetting agents and suspending agents such as those mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables, Bacterial Compositions and Kits Compositions comprising a bacterium of the invention are also provided. Examples of such bacterial compositions include, but are not limited to, starter cultures of the bacterium comprising, for example, a suitable number of bacteria in a small volume of growth or maintenance medium, compositions comprising the bacterium in the presence of a suitable stabiliser or carrier, compositions comprising the lyophilised bacterium in the presence of a suitable stabiliser carrier and compositions comprising a stab or slant of the bacteria and a suitable agar support. For probiotic use, the compositions may comprise the bacterium dispersed in a suitable foodstuff, capsule or tablet.

The present invention also provides for kits comprising a bacterium of the invention. The bacterium provided in the kit can be lyophilised and the kit can additionally contain a suitable medium for reconstitution of the lyophilised bacterium. Alternatively the bacterium may be provided as a starter culture or a stab. The kit may further comprise suitable ingredients for growth media to propagate the bacterium and/or for the fermentation of the bacterium to produce antioxidants. Individual components of the kit would be packaged in separate containers and, associated with such containers, can be instructions for use.

EXAMPLES

Example 1

Characterisation of Bacterium Accession No. 160103

Bacterial cultures and media. The new bacterium was isolated from the surface of lowbush blueberries by inoculation of Tryptic Soy Broth (Difco Laboratories, Detroit Mich.), grown at 25° C. for 36 hrs, and selected on Tryptic Soy agar. MRS and Potato Dextrose agar (Becton Dickinson and Company, Cockeysville Md.) were also used to determine the properties of the bacteria. Stock cultures were maintained at −70° C. in broth supplemented with 30% (v/v) glycerol.

Bacterial identification. Carbohydrate fermentation patterns were determined using API 50CH galleries as specified by the manufacturer (Bio Mérieux S A, Marcy-l'Étoile, France). API 20Strep and OF Medium (Bio Mérieux S A, Marcy-l'Étoile, France) were also used for bacterial characterization.

DNA methodology. The partial sequence of the 16S rRNA gene (1500 nts) was determined by MIDI Laboratories (MIDI Labs, Newark Del.) by standard procedures, and a phylogenetic analysis based on this partial 16S rRNA fragment was performed. The sequence data were compared to sequences in the Microseq® microbial analysis software and database (PE Applied Biosystems).

The 16S rRNA gene was PCR amplified from genomic DNA isolated from colonies of the novel bacterium. The primers used for the amplification correspond to positions 5, 338, 357, 515, 531, 776, 1087, 1104, 1174, 1193, and 1540 in the *E. coli* 16S rRNA gene. Amplification products were purified from excess primers and dNTPs using Microcon 100 (Amicon) molecular weight cut-off membranes and checked for quality and quantity by running a portion of the products on an agarose gel.

Cycle sequencing of the 16S rRNA amplification products was carried out using AmpliTaq FS DNA polymerase and dRhodamine dye terminators. Excess dye-labeled terminators were removed from the sequencing reactions using a Sephadex G-50 spin column. The products were collected by centrifugation, dried under vacuum and frozen at −20° C. until ready to load. Samples were resuspended in a solution of formamide/blue dextran/EDTA and denatured prior to loading. The samples were electrophoresed on an ABI Prism 377 DNA Sequencer. Data was analysed using PE Applied Biosystems DNA editing and assembly software.

Bacterial characteristics. The new bacterium isolated from lowbush blueberries was a Grain negative, catalase positive, facultatively anaerobic coccobacillus.

From the results obtained from API 50CH, the bacteria fermented D-glucose, D-fructose, D-mannose, arbutin, esculin, salicin, saccharose and D-raffinose. However, the results obtained from API 20Strep showed that the bacteria could ferment mannitol, lactose and treholase under some conditions. The bacteria also showed positive results for VP, HIP, PYRA, α Gal, β Gal, PAL and LAP activity. Results from OF Medium indicated that the novel bacterium has a fermentative metabolism. Results from the biochemical characterization and parameters of incubation for the novel bacterium are compiled in Table 1.

TABLE 1

Biochemical characterization of novel bacterium

| Characteristic or test | Reaction[a] |
|---|---|
| Growth on: | |
| TSA at: | |
| 10° C. | + |
| 15° C. | + |
| 25° C. | + (optimum) |
| 35° C. | + |
| 37° C. | − |
| PDA | + |
| MRS | − |
| Simmons Citrate Agar | + |
| Voges-Proskauer test | + |
| OF glucose | + |
| Catalase | + (strong) |
| Acidification in the presence of: | |
| Glycerol | − |
| Erythritol | − |
| D-arabinose | − |
| L-arabinose | − |
| Ribose | − |
| D-xylose | − |
| L-xylose | − |

TABLE 1-continued

Biochemical characterization of novel bacterium

| Characteristic or test | Reaction[a] |
|---|---|
| Adonitol | − |
| β-methyl-D-xyloside | − |
| Galactose | − |
| D-glucose | + |
| D-fructose | + |
| D-mannose | + |
| L-sorbose | − |
| Rhamnose | − |
| Dulcitol | − |
| Inositol | − |
| Mannitol | + |
| Sorbitol | − |
| α-methyl-D-mannoside | − |
| α-methyl-D-glucoside | − |
| N-acetyl-glucosamine | − |
| Amygdalin | − |
| Arbutin | − |
| Esculin | + (strong) |
| Salicin | + |
| Cellobiose | − |
| Maltose | − |
| Lactose | + |
| Melibiose | − |
| Sucrose | + |
| Trehalose | + |
| Inulin | − |
| Melezitose | − |
| D-Raffinose | + |
| Starch | − |
| Gycogen | − |
| Xylitol | − |
| β-gentiobiose | − |
| D-turanose | − |
| D-lyxose | − |
| D-tagatose | − |
| D-fucose | − |
| L-fucose | − |
| D-arabitol | − |
| L-arabitol | − |
| Gluconate | − |
| 2-keto-gluconate | − |
| 5-keto-gluconate | − |
| Enzyme production: | |
| β-glucosidase | + |
| pyrrolidonyl arylamidase | + |
| α-galactosidase | + |
| β-glucuronidase | − |
| β-galactosidase | + |
| alkaline phosphatase | + |
| leucine arylamidase | + |
| arginine dihydrolase | − |
| Hydrolysis of hippurate | + |

[a]+, positive; −, negative

The biochemical profile and 16S rRNA gene sequence of the novel bacterium indicate that it comes from the family of facultatively anaerobic gram-negative rods, Enterobacteriaceae. Bacteria from this family have both a respiratory and fermentative type of metabolism and are catalase positive and oxidase negative.

Sequence of the 16S rRNA gene sequence for the bacterium is shown in FIG. 1 (SEQ ID NO:1), and was compared to sequences in the Microseq™ microbial analysis software and database. The top ten alignment matches are presented in a percent genetic distance format. A low percent indicates a close match. Also provided for the bacterium are neighbour joining phylogenetic trees (Saitou and Nei, 1987, *Mol. Biol. Evol.*, 4, 406-425), generated using the top ten alignment matches (FIG. 2).

Genetic relationships are expressed in the form of Percent Genetic Differences (% GD). A species level match may be assigned if the % GD between the unknown and the closest match is less than the approximate average % GD between species within that particular genetic family, which is usually 1% (Palys et al., 1997, *IJSB*, 47, 1145-1156), but can be up to 3% (see, Vandamme, et al., (1996) *Microbiol. Reviews* 60:407-48; Kolbert & Persing, (1999) *Curr. Microbiol*, 2:299-305). A genus level match will be assigned when the sequence does not meet the requirements for a species level match, but still clusters within the branching of a well-defined genus. For the novel bacterium, its closest match was *Serratia proteamaculans quinovora*, the % GD determined was 1.82%, which was more than the average % GD of 1.28% between species within the family of Enterobacteriaceae. The % GD for other bacterial species were as follows:

| | |
|---|---|
| *Serratia grimesii* | 1.85% |
| *Serratia plymuthica* | 1.95% |
| *Hafnia alvei* | 1.95% |
| *Serratia proteamaculans proteamaculans* | 2.05% |
| *Ewingella americana* | 2.47% |
| *Serratia ficaria* | 2.47% |
| *Serratia fonticola* | 2.51% |
| *Serratia entomophila* | 2.73% |
| *Yersinia frederiksenii* | 2.83% |

The positive result obtained in the Simmons Citrate test and the fermentation of raffinose and sucrose by the bacterium indicates that it is not from the genus *Hafnia* (Holt and al., 1994, supra). Moreover, the novel bacterium presents only 94% identity with *Hafnia alvei*, compared to 97% of identity with *Serratia proteamaculans quinovora*, when the 16S rRNA gene partial sequence are analysed by BLAST 2. However, the bacterium does not ferment maltose and ribose, which is fermented by all strains of *Serratia*. In addition, comparison of novel bacterium 16S rRNA partial sequence with GenBank indicates that a *Rahnella* genospecies is the closest match with 98% identity to the 16S rRNA partial sequence. However, the biochemical profile of novel bacterium does not match the one of *Rahnella*, which demonstrates acid production from L-arabinose, cellobiose, maltose, melibiose, D-sorbitol and D-Xylose (Holt and Krieg, 1984, *Bergey's. Manual of Systematic Bacteriology*, Vol. 1, Williams and Wilkins Co., Baltimore, pp. 1-964).

Example 2

Increase in Antioxidant Capacity of Blueberries During Fermentation with the Bacterium (Accession No. 160103)

Chemicals. Gallic acid was purchased from Acros (New Jersey, USA). Quercetin, rutin, chlorogenic acid, p-coumaric acid and sinapic acid were purchased from Sigma-Aldrich Canada Ltd. (Ontario, Canada).

Growth of bacteria. Studied bacteria were grown in Tryptic Soy Broth (Difco Laboratories) for 24 hrs, at 22° C. Samples of the microflora of blueberries were also plated on MRS Agar (BDH) in order to characterize the microorganisms contained therein. Stock cultures were maintained at −70° C. in Tryptic Soy Broth supplemented with 30% (v/v) glycerol.

Preparation of blueberry mixture. Wild blueberries harvested from different areas of the Atlantic region were mixed equally to reduce the possibility of local variations in the fruit microflora. The mixture was prepared by blending the blueberries in a Braun Type 4259 food processor with an equivalent volume (1:1 v/v ratio) of Minimal Broth Davis without dextrose (Difco laboratories). The blueberry mixture was then centrifuged at 1700 RPM for 6 min in an IEC Centra MP4R centrifuge (international Equipment Company) to remove non homogenized particles. The resulting blueberry juice was sterilized by filtration under vacuum through a 0.22 µm Express Millipore filter apparatus (Millipore). The blueberry juice was then inoculated with a saturated culture of the novel bacterium. The quantity used was 1% of the total blueberry juice volume, For each flask that was inoculated, a control flask was prepared under the same conditions but without inoculation. The control contained 1% of total blueberry juice volume of sterilized Tryptic Soy Broth (Difco Laboratories) in place of the bacterial culture.

Fermentation. The blueberry media were incubated in a Lab-Line low temperature bench top incubated shaker (Lab-Line Instruments, Inc.) at 22° C. and 120 RPM for up to 7 days. Fermentations were first made with the normal flora of blueberry by inoculation with 1% of saturated TSB culture obtained from inoculation by whole blueberries. Then, fermentations were made with the novel bacterium isolated from TSA. A controlled fermentation without inoculation was made in a 2.5 Liter BIOFLO 3000 fermentor (New Brunswick Scientific) by simulating pH variation with addition of acetic acid 4N and NaOH 4N.

Sampling. Samples were taken at various times during the experiment and filtered through 0.22 µm Millex-GP filters (Millipore). They were then frozen at −20° C. until further analysis. During each sampling, the pH level was measured with an AR15 Accumet pH meter (Fisher Scientific) and the total soluble solids were measured with an Atago Model N1 hand refractometer. A microbial count was performed for each sample on Tryptic Soy Agar Difco Laboratories) using sterilized peptone water as dilution medium. The colonies were numbered after 48 hrs of incubation at 22° C.

Phenolic compounds. The samples were analyzed using the Folin-Ciocalteu method for measurement of total phenolics. Gallic acid was used as a calibration standard. The prepared samples were read by a µQuant Microplate Reader (Bioteck instrument Inc.) set at a wavelength of 700 nm.

Determination of Radical Scavenging Activity. Antioxidant capacity was tested using 2,2-Diphenyl-1-picrylhydrazyl (DPPH) as a stable radical. DPPH in methanol 80% (150 µM, 200 µL) was added to 22 µL of the test compounds at different concentrations (0-500 µM) in methanol. Each mixture was then shaken and incubated at room temperature and in the dark. The decrease in absorbance of DPPH was measured at 30, 180 and 360 minutes of incubation at 520 nm in a µQuant Microplate Reader (Bioteck Instrument Inc.). Methanol was used as a blank solution. DPPH solution (200 µL) in ethanol (22 µL) served as the control. All tests were performed in triplicate.

A plot of $A_{520\,nm}$ versus concentration of sample in the final solution was made for each time interval. Using the results from the time interval with the steepest slope, the initial slope of the curve was calculated by linear regression ($r^2$>0.800). The antiradical activity was defined by the initial slope value in units of $A_{520\,nm}$/µM of sample or µM of DPPH/µM of sample. The units were converted from $A_{520\,nm}$ to µM of DPPH by developing a standard curve for DPPH using the microplate reader. The concentration of DPPH was initially determined from the calibration curve equation given by Brand-Williams et al. (1995, *Lebensm. Wiss. Technol.*, 28:25-30), where $A_{515\,nm}$ was equal to 12509×concentration of DPPH in M-0.00258. The antiradical activity was found to be equivalent to negative half of the antiradical power (ARP) as previously defined (Brand-Williams et al. 1995, Ibid). ARP was equal to the reciprocal of the amount of compound required to decrease the initial DPPH concentration by 50% in units of moles of DPPH per mole of sample.

Separation by Capillary Electrophoresis. A capillary electrophoresis system from Hewlett Packard, model G1600AX, was used for comparison of phenolic profiles between non-fermented and fermented blueberry samples. A 64.5 cm total length, 56.0 cm effective length and 50 µm i.d. bubble factor 3 PVA coated capillary with optical path length of 150 µm (Agilent Technologies, Inc.) was used for the separation. Samples were injected using 50.0 mbar pressure, for 30.0 seconds. The separation was made using borate 50 mM pH 9.25 as buffer, under maintained temperature of 25° C., and voltage of 25 kV set at positive polarity, and current to 120 µA. Detection of compounds was made using diode array detection at 280, 345, 520 and 200 nm.

Quantification of the phenolic acid compounds by HPLC. The method used to separate the phenolic compounds on HPLC was derived from Kalt and al. (1999, *Can. J. Plant Sci.*, 79:617-623). A 50 µL injection of sample was separated on a Zorbax SB-C18 Rapid Resolution 4.6 mm i.d.×150 mm, 3.5 µm associated to a ODS-Hypersil (C-18) guard column 2.1 mm i.d.×20 mm, 5 µm from Agilent Technologies Inc. using a Agilent HPLC 1100 series system equipped with a quaternary pump and a Diode Array Detector. Data were collected at 270 nm, 520 nm, 340 nm, 320 nm, and 365 nm, with 800 nm set as reference. Compounds were separated with 5% formic acid in water (solvent B) and methanol (solvent D), using a gradient elution program; 0-10.24 min, 14-17% D; 10.24-35.28 min, 17-23% D; 35.28-64.59 min, 23-47% D; 64.59-66.59 min, 47-14% D; 66.59-70 min, 14% D. Flow rate was 1.0 mL min$^{-1}$.

Column temperature was maintained at 30° C. during separation. Samples were filtered through a 0.22 µm Millex-GP filter unit (Millipore, Canada) prior to injection. HPLC quantification was made by comparison with gallic acid as reference for comparison between peak heights.

Statistical Analysis. Data: represent the mean of three replicate analyses tested. Results were processed for statistical significance using Student's t test. Differences at P<0.05 were considered to be significant.

Fermentation with fruit surface microflora. An increase in total phenolic content from fermentation was obtained with the fruit normal flora of wild blueberries (Table 2). Fermentation conditions were 22° C., 120 RPM and an aerobic environment. The decrease in pH of the medium and an increase in bacterial plate counts on TSA were in concordance with the increase in total phenolics during fermentation. Total soluble solids, as indicated by the °Brix, decreased during fermentation. On day 3, numerous bacteria were isolated from TSA plate counts to find one bacterium that would be responsible for the increase in phenolic content. These bacteria were then tested in fermentation to determine their effect on the total phenolic content of wild blueberry samples.

TABLE 2

Results obtained during fermentation of wild blueberry by the normal microflora found on fruit surface.

| Time (days) | Bacterial counts | °Brix | pH | Total phenolics$^a$ |
|---|---|---|---|---|
| 0 | 4 | 6.1 ± 0.2 | 4.74 ± 0.03 | 166.84 ± 22.86 |
| 1 | 2.0 × 10$^2$ | 6.1 ± 0.1 | 4.47 ± 0.01 | 99.36 ± 10.70 |
| 3 | 3.5 × 10$^8$ | 6.0 ± 0.1 | 3.66 ± 0.04 | 176.57 ± 6.65 |

TABLE 2-continued

Results obtained during fermentation of wild blueberry by the normal microflora found on fruit surface.

| Time (days) | Bacterial counts | °Brix | pH | Total phenolics$^a$ |
|---|---|---|---|---|
| 5 | 2.8 × 10$^7$ | 4.0 ± 0.1 | 3.32 ± 0.04 | 409.32 ± 84.52 |
| 7 | ND | 3.1 ± 0.1 | 3.35 ± 0.07 | 372.46 ± 45.11 |

$^a$Total phenolics are expressed in mg of gallic acid equivalent/100 g of fresh weight.
ND indicates not determined Fermentation with the bacterium. Fermentation was conducted in the presence of the bacterium at 22° C., 120 RPM under aerobic conditions. To prevent phenolic degradation by heat, filtration through 0.22 µm filters was used as a method of sterilizing the juice. A control fermentation was conducted under the same conditions, but using an inoculum of sterile TSB. Negative controls were run under the same conditions. A noticeable increase in the total phenolic content of wild blueberry juice occurred after only 1 day of incubation, indicating that the bacterium plays an important role in the increase of total phenolic content (Table. 3). Total soluble solids, as demonstrated by the °Brix, decreased from day one (6.40±0.05) to day seven (3.87±0.11) of fermentation. An interesting-phenomenon during fermentation was PH variation. The pH changed from day one (4.73±0.01) to reach the lowest point on day 3 (3.31±0.05), followed by an increase on day 7 (5.09±0.17). The increase in pH was concomitant with a decrease in bacterial count. No significant variation in total phenolics, pH and °Brix was observed for the controlled fermentation.

A control fermentation conducted using standard Medium in place of the berry juice medium did not result in any increase in phenolic antioxidant content of the medium.

Figure 3:
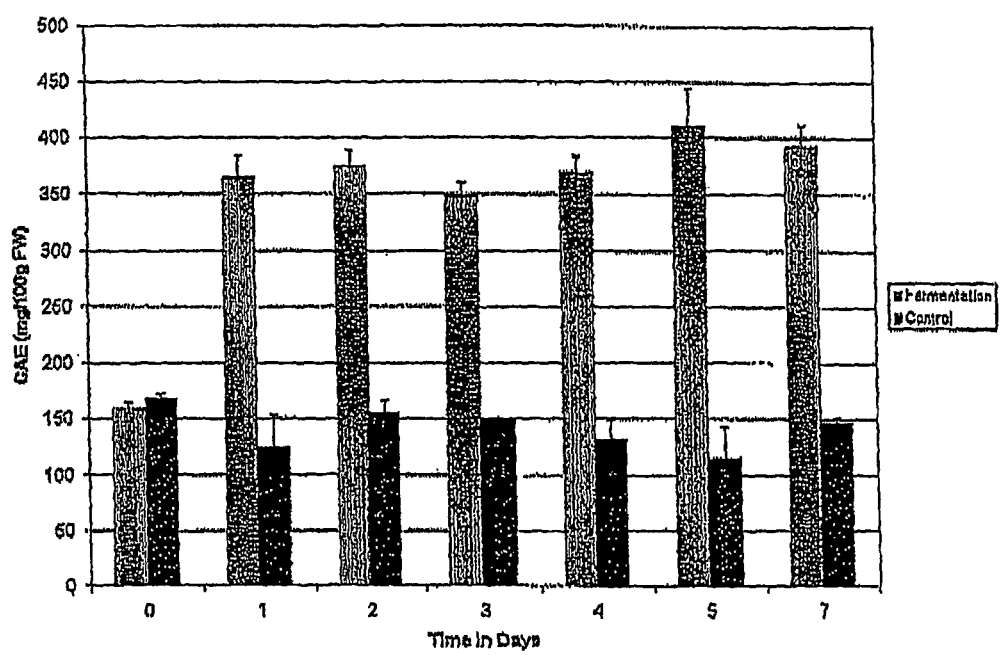
FIG. 3 depicts the total phenolic content in GAE (mg of gallic acid equivalent/100 g of fresh weight), during fermentation of blueberry by the bacterium (Accession No. 160103). Error bars indicate standard deviation for each day of fermentation.

A fermentation simulation was conducted to study the effect of pH variation on phenolic content. This fermentation involved a sterilized blueberry medium in which the pH was adjusted over time by addition of acetic acid and sodium hydroxide to simulate the pH variation that occurred during fermentation with the novel bacterium. No significant variation in total phenolic content was observed during the 6 days that the fermentation simulation was conducted (see, FIG. 3 and Table 3).

TABLE 3

Total phenolic content during fermentation of wild blueberry by the bacterium.

| Day of Fermentation | Total Phenolic Content (mg of gallic acid equivalent/100 g of fresh weight) | | |
|---|---|---|---|
| | Control | Fermentation | pH Simulation |
| 0 | 168.25 ± 3.55 | 158.12 ± 4.88 | 105.27 ± 1.99 |
| 1 | 125.13 ± 27.87 | 364.03 ± 20.11 | 98.98 ± 4.48 |
| 2 | 154.19 ± 11.91 | 374.66 ± 14.64 | 90.71 ± 2.69 |
| 3 | 150.75 ± 3.77 | 347.94 ± 12.00 | 102.63 ± 12.19 |
| 4 | 132.16 ± 16.36 | 369.03 ± 14.47 | 98.53 ± 0.93 |
| 5 | 115.59 ± 26.91 | 410.59 ± 33.44 | 99.36 ± 2.94 |
| 7 | 147.00 ± 4.46 | 392.63 ± 19.43 | 101.44 ± 3.89 |

Figure 4:
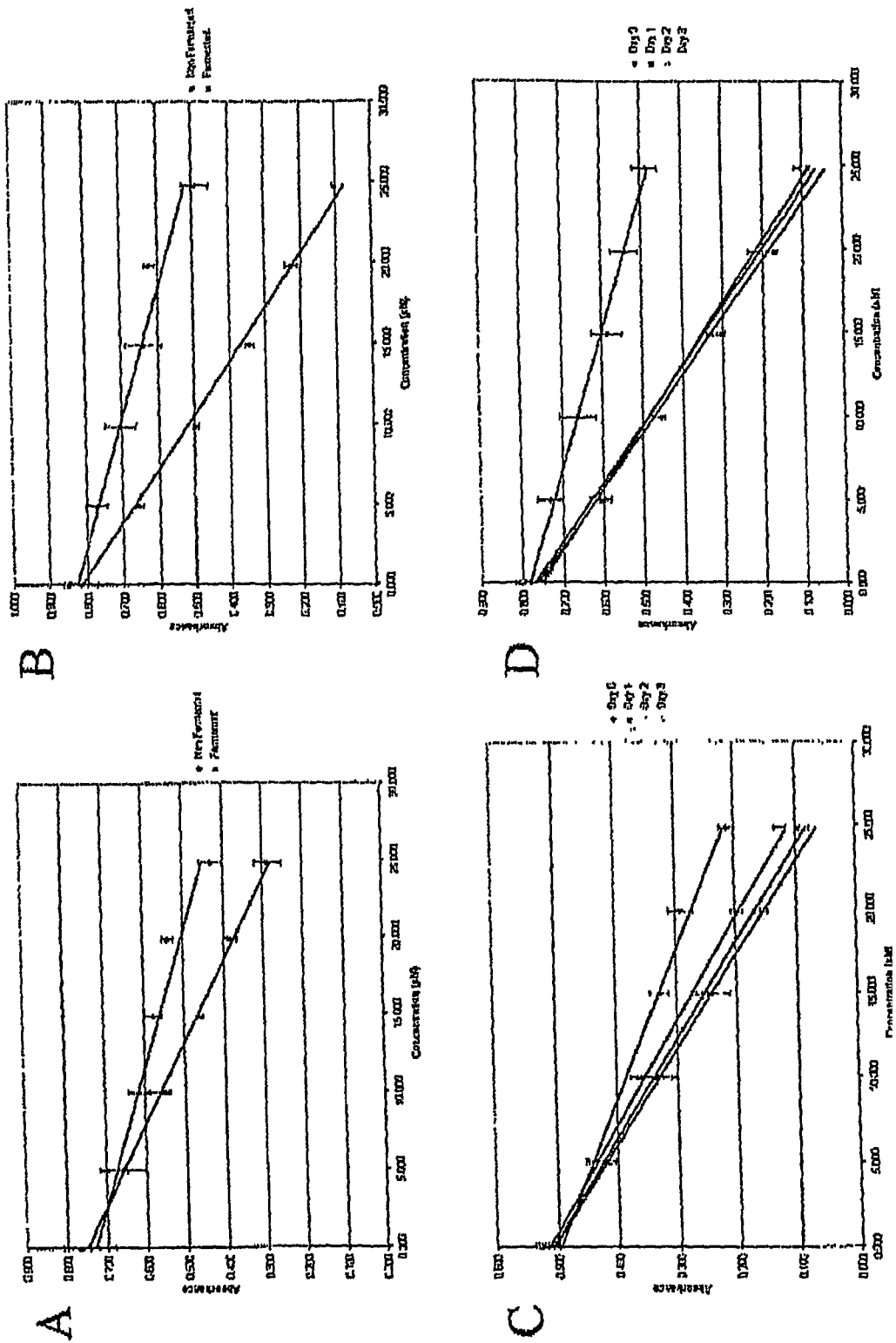
FIG. 4 depicts the difference in radical scavenging activity (RSA) between non-fermented and fermented blueberry juice samples after 3 days of fermentation with (A) same total phenolic concentration and (B) different total phenolic concentration. Increase in RSA over time for (C) non-fermented blueberries and (D) fermented blueberries.

Radical Scavenging Activity. Samples collected from the blueberry fermentation with the bacterium were assessed for radical scavenging activity (RSA) using the DPPH method (FIG. 4). Such analysis has been previously associated with the study of antioxidant capacity (Brand-Williams, W., et al., (1995) *Lebensm. Wiss. Technol.*, 28, 25-30). Increase in RSA was not only associated with an increase in total phenolic content during fermentation, but also with a change in the phenolic profile, resulting in the production of phenolic compounds with better antioxidant capacity, as shown in FIGS. 4A and 4B. However, during the first three days of fermentation, the increase in RSA for day 1 and 2 was followed by a decrease for day 4 (FIGS. 4C and 4D). This increase in RSA was not only associated with the increase in total phenolic content, but also with a change in the phenolic profile of fermented blueberry. In contrast, the loss in RSA on day 3, of the fermentation can be attributed to an alteration of the phenolic profile, but not to a loss in total phenolics (FIGS. 4C and 4D). Another way to present the RSA, is by the antiradical activity and antiradical power, indicative of the antioxidant capacity (Tables 4 and 5). These results were calculated from results obtained from the DPPH method.

TABLE 4

Antiradical activity of fermented blueberry samples for DPPH radical (total phenolic concentrations being adjusted to the initial value of the samples)

| Blueberry sample | Antiradical activity[a] | Antiradical power[b] |
|---|---|---|
| Non fermented after 3 days | −1.985 ± 0.349 | 3.970 |
| After 3 days of fermentation | −3.367 ± 0.237 | 6.733 |
| Day 0 of fermentation | −2.904 ± 0.124 | 5.809 |
| Day 1 of fermentation | −4.437 ± 0.062 | 8.874 |
| Day 2 of fermentation | −4.599 ± 0.022 | 9.197 |
| Day 3 of fermentation | −4.176 ± 0.183 | 8.352 |

[a]Values are means of slope coefficients calculated by linear regression ± standard deviations (n = 3) in μM of DPPH/μM of blueberry sample in GAE.
[b]Antiradical power was defined as the reciprocal of the amount of antioxidant needed to decrease the initial DPPH concentration by 50%. The antiradical activity was equivalent to the negative half of the antiradical power.

TABLE 5

Total phenolic concentrations not adjusted to the initial value of samples

| Blueberry sample | Antiradical activity[a] | Antiradical power[b] |
|---|---|---|
| Non fermented after 3 days | −2.021 ± 0.269 | 4.042 |
| After 3 days of fermentation | −4.857 ± 0.060 | 9.714 |
| Day 0 of fermentation | −2.076 ± 0.352 | 4.152 |
| Day 1 of fermentation | −4.954 ± 0.049 | 9.909 |
| Day 2 of fermentation | −4.849 ± 0.071 | 9.699 |
| Day 3 of fermentation | −4.606 ± 0.109 | 9.211 |

[a]Values are means of slope coefficients calculated by linear regression ± standard deviations (n = 3) in μM of DPPH/μM of blueberry sample in GAE.
[b]Antiradical power was defined as the reciprocal of the amount of antioxidant needed to decrease the initial DPPH concentration by 50%. The antiradical activity was equivalent to the negative half of the antiradical power.

Figure 5:
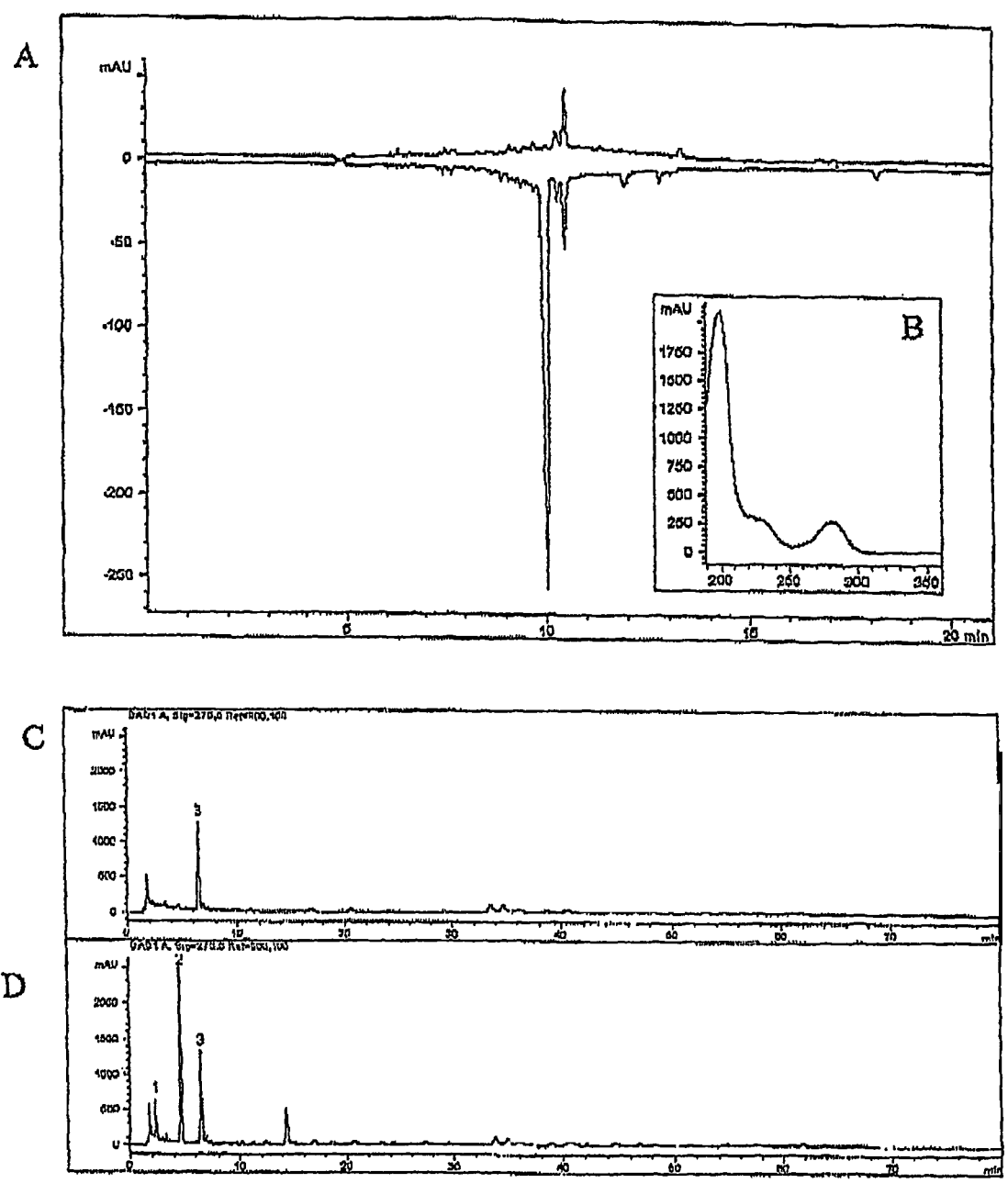
FIG. 5 depicts the phenolic profiles derived using (A) capillary electrophoresis for separation, and diode array detection at 280 nm of unfermented (positive signal) and fermented (negative signal) blueberry samples. (B) The UV spectrum of the main peak obtained from fermented blueberry sample. HPLC derived phenolic profiles are depicted for (C) unfermented blueberry and (D) fermented blueberry samples. Peaks of interest are: (1) gallic acid; (2) unknown phenolic acid; (3) chlorogenic acid.

Sample separation by capillary electrophoresis. Phenolic profiles for blueberry fermented with the bacterium and the control fermentation were determined by capillary electrophoresis (EC) in order to identify any major changes (FIG. 5A). From the EC results, the increase in total phenolics during fermentation could be attributed to the production of a particular phenolic compound, as shown by the presence of a main peak on the phenolic profile of fermented blueberry. UV spectra of the main peak, as shown in FIG. 5B, is characterized by a strong absorbance at 200 nm, followed by a plateau from 215 nm to 235 nm, and a second strong absorbance at 280 nm. The UV spectra for this compound confirmed that it was not a flavonoid structure, such as an anthocyanin or a flavonol, because of the absence of absorbance peaks in the 520 nm and 350 nm regions, respectively, and, therefore, is likely to be of the phenolic acid type.

Quantification and characterization of phenolic acid compounds by HPLC. HPLC was also used to characterize the phenolic acid compounds obtained from fermented blueberry sample with bacterium. Quercetin could not be detected from phenolic profiles of non-fermented and fermented blueberry samples by HPLC spiking. However, rutin could be detected at an approximate concentration of (1.22±0.02) mg/100 g FW in non-fermented blueberry samples after 3 days of incubation. Significant decrease in rutin content to (1.09±0.03) mg/100 g FW could be observed in fermented blueberry samples with the same incubation time (P<0.05). Production of gallic acid has been observed during blueberry fermentation, as shown by HPLC spiking. Gallic acid went from a non-detectable concentration on day 0 to a concentration of (6.46±0.05) mg/100 g FW on day 3 of blueberry fermentation peak 1, FIG. 5D). However, gallic acid concentration varied from one fermentation to the other, and could be as low as (2.67±0.09) mg/100 g FW after 3 days of fermentation. Increase in gallic acid content could be attributed to hydrolysable tannin degradation during the fermentation process. Content of chlorogenic acid after 3 days of blueberry fermentation was (85.27±0.28) mg/100 g FW. No significant difference could be observed in the chlorogenic acid concentration between fermented and unfermented blueberry (P<0.05) (peak 3, FIGS. 5C and D). No p-coumaric acid and sinapic acid were detected in any of the fermented and unfermented blueberry samples. Peak 2 (FIG. 5D) was produced only after fermentation of blueberry with the bacterium at a concentration of (64.20±0.13) mg of gallic acid equivalents/100 g FW after 3 days of incubation. No significant variation was observed between day 1 and day 5 of fermentation for concentration of the new compound (P<0.05).

From results obtained in his example, it was concluded that increase in antioxidant capacity during fermentation was not only attributed to increase in total phenolics, but also to a change in the phenolic profile as shown by HPLC.

Overall, it was found that the bacterium isolated from the normal surface micro-flora of blueberry is mainly responsible for the increase in total phenolics observed during fermentation by the normal micro-flora found on the fruit surface. Fermentation by this bacterium also increases the antioxidant capacity of blueberries, as demonstrated by the radical scavenging activity, not only from increase in total phenolics, but also from a change in the phenolic profile, as demonstrated by the production of gallic acid and other compounds.

Example 3

Increase in Antioxidant Capacity of Cranberries During Fermentation with the Bacterium (Accession No. 160103)

Preparation of cranberry mixture. Cranberries were purchased from Canneberges Acadiennes (Richibouctou Village, NB) and the resulting cranberry mixture was produced utilizing the method described in the preceding example, with minor modifications. The quantity of saturated culture of the bacterium utilized to inoculate the juice was 2% of the total juice volume. For each flask that was inoculated, a control flask was prepared under the same conditions, but using 2% of the total juice volume of sterilized Tryptic Soy Broth in place of the bacterial inoculum.

Fermentation The cranberry juice media was fermented with the bacterium as described in example 2, for up to 4 days.

Sampling and Analysis of total phenolics, radical scavenging activity and HPLC were performed as described in the preceding example.

Figure 7:
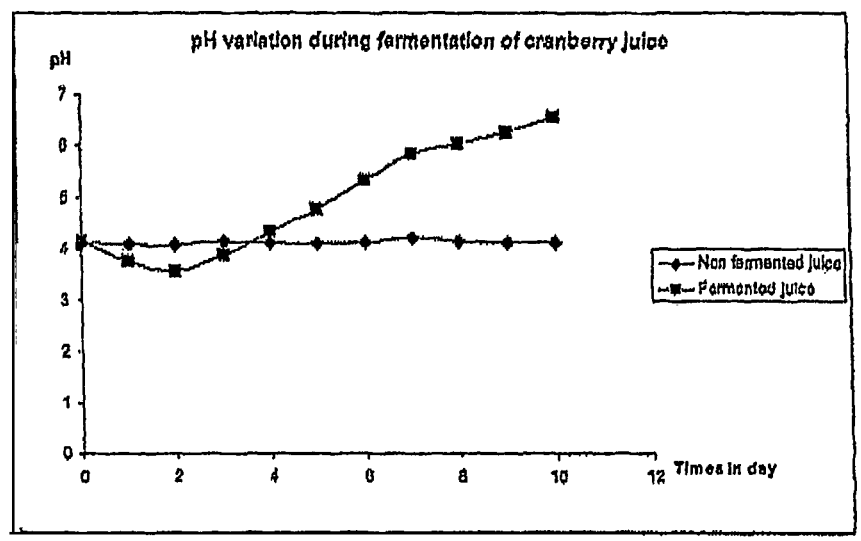
FIG. 7 depicts pH variation during cranberry juice fermentation by the bacterium (Accession No. 160103).

Fermentation with the bacterium. Fermentation of cranberry juice was conducted in the presence of the bacterium under aerobic conditions and resulted in a noticeable increase in the total phenolic content of the fermented cranberry juice after only 1 day of incubation, indicating that the bacterium plays an important role in the increase of total phenolic content. (FIG. 6A). An interesting phenomenon during fermentation was pH variation (FIG. 7). Cranberry juice pH decreased from 4.13 to the minimum value 3.56 after 2 days of fermentation and increased to 6.54 by the $10^{th}$ day of fermentation. The mixture colour changed simultaneously with the pH, from dark red at the beginning to light rose, dark green, brown and black at the end. This pH variation affected the phenolic content of fermented cranberry juice.

Fermentation with the bacterium under anaerobic conditions. Similar fermentation was conducted under anaerobic conditions in a 2.5 Liter BIOFLO 3000 fermentor (New Brunswick Scientific). The phenolic content of fermented cranberry juice increased under anaerobic conditions (FIG. 8A).

Fermentation with the novel bacterium and wine yeast (*Saccharomyces cerevisiae*). Fermentation of cranberry juice was conducted in the presence of the bacterium and wine yeast under anaerobic conditions. The phenolic content of the fermented cranberry juice also increased under these conditions (FIG. 8B). This experiment demonstrated the compatibility of the bacterium with *Saccharomyces cerevisiae*.

Figure 9:
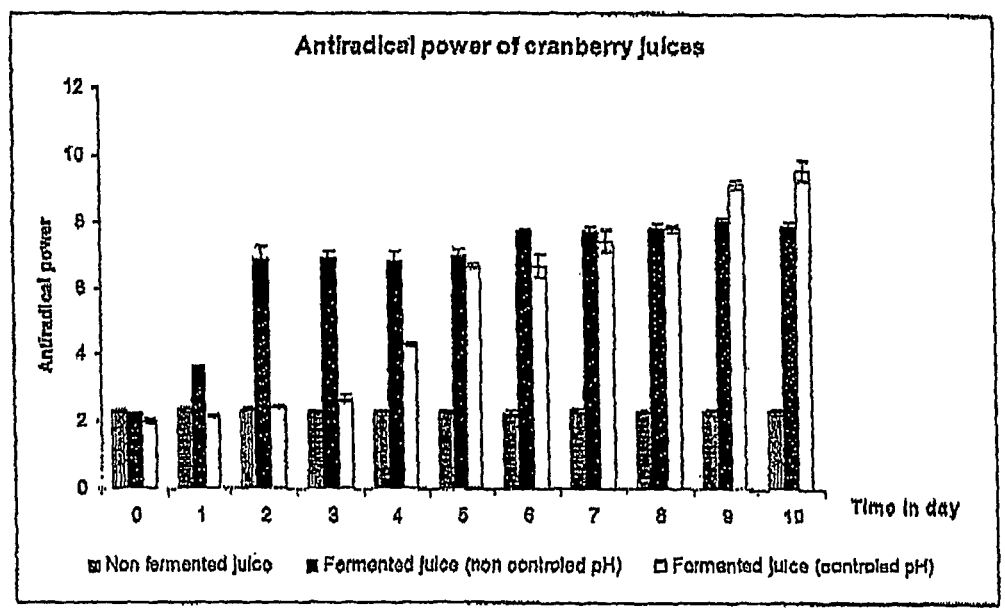
FIG. 9 depicts the antiradical power of unfermented and fermented cranberry juice by the bacterium (Accession No. 160103).

Radical scavenging activity. Samples collected from the cranberry juice fermentation with the bacterium were studied for radical scavenging activity (RSA), using the DPPH method as described in the preceding example. Another way to present the RSA is by the antiradical activity and antiradical power, indicative of the antioxidant capacity (FIG. 9). These results were calculated from data obtained by the DPPH method. Table 6 shows antiradical activity as translated from the DPPH method.

TABLE 6

The antiradical activity and antiradical power of cranberry juice

| Extract | Antiradical activity | Antiradical power |
|---|---|---|
| Unfermented cranberry juice | | |
| Day 0 | −1.15 (0.02) | 2.30 (0.06) |
| Day 1 | −1.17 (0.03) | 2.34 (0.06) |
| Day 2 | −1.18 (0.02) | 2.37 (0.04) |
| Day 3 | −1.16 (0) | 2.33 (0) |
| Day 4 | −1.14 (0.02) | 2.29 (0.04) |
| Day 8 | −1.16 (0.04) | 2.31 (0.09) |
| Day 9 | −1.14 (0.05) | 2.29 (0.11) |
| Day 10 | −1.15 (0.03) | 2.30 (0.06) |
| Fermented cranberry juice (pH not controlled) | | |
| Day 0 | −1.12 (0) | 2.25 (0) |
| Day 1 | −1.82 (0.02) | 3.65 (0.05) |
| Day 2 | −3.43 (0.20) | 6.86 (0.39) |
| Day 3 | −3.47 (0.09) | 6.94 (0.19) |
| Day 4 | −3.41 (0.15) | 6.82 (0.29) |
| Day 8 | −3.91 (0.07) | 7.82 (0.14) |
| Day 9 | −4.02 (0.04) | 8.04 (0.08) |
| Day 10 | −3.95 (0.08) | 7.89 (0.16) |
| Fermented cranberry juice (controlled pH) | | |
| Day 0 | −1.01 (0.03) | 2.01 (0.06) |
| Day 1 | −1.09 (0.02) | 2.18 (0.05) |
| Day 2 | −1.22 (0.03) | 2.44 (0.06) |
| Day 3 | −1.33 (0.05) | 2.65 (0.11) |
| Day 4 | −2.15 (0.02) | 4.30 (0.05) |
| Day 8 | −3.90 (0.05) | 7.89 (0.11) |
| Day 9 | −4.58 (0.06) | 9.16 (0.13) |
| Day 10 | −4.78 (0.16) | 9.56 (0.31) |
| Gallic acid* | −6.21 (0.60) | 12.50 |
| Chlorogenic acid* | −5.08 (0.29) | 10.16 |

*Fukumoto and Mazza (2000)

Quantification and characterization of phenolic acid compounds by HPLC. HPLC was used to analyze the changes in phenolic profiles of fermented cranberry juice as previously described with blueberry juice. Quercetin, Rutin, Chlorogenic acid, Sinapic acid, and p-coumaric acid were used to determine their content in non fermented and fermented cranberry juices by HPLC spiking. Unlike blueberry juice, none of these compounds were detected with the HPLC method used (data not shown). Production of gallic acid was observed during cranberry fermentation, as shown by HPLC spiking.

Example 4

Effects of Fermented Cranberry and Blueberry Juices on the Inhibition of Nitric Oxide Production Preparation of blueberry and cranberry mixture. The blueberry and cranberry mixtures were produced utilizing the methods described in the preceding examples. Briefly, the quantity of saturated culture of the bacterium utilized: to inoculate the juice was 2% of the total juice volume. For each flask that was inoculated, a control flask was prepared under the same conditions, but without inoculation. Instead, a quantity of 2% of the total juice volume of sterilized Tryptic Soy Broth was added to the mixture.

Fermentation The blueberry and cranberry juice media were fermented with the novel bacterium as described in the preceding examples, for up to 4 days.

Cell culture. The mouse monocyte/macrophage cell line RAW 264.7 gamma NO(−) [American Type Culture Collection (ATCC)] was cultured in RPMI-1640 supplemented with 10% (v/v) heat-inactivated PBS, streptomycin (100 mg/ml) and penicillin (100 units/ml). All cultures were incubated at 37° C. in a humidified atmosphere with 5% $CO_2$. Cell number was assessed by trypan blue dye exclusion on a Neubauer hemacytometer. Cells were grown to 90% confluence in sterile cell culture flasks and gently detached using a scraper (Fisher Scientific). For phenolic compound treatment tests, cells were cultured in triplicate in Costar flat-bottom cell culture plates (Corning Inc.). Cells were plated at a density of $6 \times 10^5$ cells/well in 24-well cell culture plates and grown for 1 h to allow them to attach to the plate. Compounds to be tested were initially dissolved in 10 µl of DMSO, and then RPMI was added to make solutions in a series of concentrations with a dilution factor of 2. The final concentrations of test compound that cells received were 16, 31, 63, 125, 250, and 500 µM, respectively. For berry juices, the final concentrations were 16, 31, 63, 125, 250 and 500 µM GAE, respectively. Cells were supplemented with the test compounds for 1 h before stimulation with 10 ng/ml lipopolysaccharide (LPS) and 10-50 units/ml interferon gamma (IFN-γ). The activated cells were incubated for 24 h and then supernatants were collected to determine nitrite concentration and/or stored at −80° C. for further use. Control cells were grown under identical conditions but were not exposed to the test compounds or LPS/IFN-γ.

Nitric Oxide (NO) Determination. Nitrite concentration was used as an indication of NO production. The procedure for NO determination was based on the Griess reaction. The assay was assessed as in the methods of Wang and Mazza (2002a, 2002b) for cell supernatants supplemented with phenolic compounds or berry juices. In brief, 100 µL of cell culture supernatant or sodium nitrite standard was mixed with an equal volume of Griess reagent [a mixture of 0.1% (w/v) N-(1-naphthyl)-ethylenediamine dihydrochloride and 1% (w/v) sulfanilamide in 5% (v/v) phosphoric, acid, the two parts being mixed together within 1 h of use] using a 96-well plate. A set of parallel analyses was also conducted by applying only 100 µL of 2.5% (v/v) phosphoric acid instead of Griess reagent to each of 100 µL of cell supernatants or the mixture of standard sodium nitrite and cyanidin chloride. After 20 min at room temperature, the absorbance at 540 nm was measured using the microtitration reader. The net absorbance of the product of the Griess reaction was obtained by subtracting that of anthocyanins from the total. The absorbance was referred to a nitrite standard curve to determine the nitrite concentration in the supernatants.

Cell Viability. Cell viability was determined by the MTT assay and/or the resazurin-based in vitro toxicology assay kit, TOX-8 (Sigma). The viability of cells activated only by LPS/IFN-γ was arbitrarily set as 100, and all other viabilities, that is, cells receiving different treatments but within the same 24-well plate, were normalized to that of the LPS/IFN-γ activated control cells.

Tumour necrosis factor alpha (TNF-α) Quantification. TNF-α in cell supernatants was determined by using an OptELISA set mouse TNF-α (mono/poly) from BD PharMingen. The enzyme-linked immunosorbent assay (ELISA) was carried out as specified by the manufacturer.

Statistical Analysis. Data represent the mean of three replicate analyses tested. Results were processed for statistical significance using Student's t test. Differences at P<0.05 were considered to be significant.

Inhibition of Nitric Oxide Production. RAW 264.7 gamma NO(−) cell line was derived from the RAW 264.7 mouse monocyte/macrophage cell line. Unlike the parental line, RAW 264.7 gamma NO(−) does not produce nitric oxide upon treatment with IFN-γ alone, but requires LPS for full activation. When LPS/IFN-γ was administered to RAW 264.7 gamma (NO-) macrophages, NO production, measured as nitrite, increased dramatically from the basal level of 0 to ≥30 µM after 24 h. To determine the effects of cranberry and blueberry juice and other phenolic compounds on NO production, different concentrations of these compounds (500, 250, 125, 63, and 16 µM) were incubated with the LPS/IFN-γ-activated macrophages (Table 7). Cell viability was assayed to exclude the possibility that the inhibitory effects of phenolic compounds were due to their cytotoxicity. The MTT assay was used for the colorless phenolic compound-treated macrophages, whereas the resazurin assay was used for cranberry and blueberry juice-treated macrophages.

The inhibitory effects (IE) was expressed as the percentage decrease of NO production as $$IE\ (\%) = 100 - [NO]^a / [NO]^b \times 100$$

Where $[NO]^a$ represents the NO concentration in supernatants from both phenolic compounds supplemented and LPS/IFN-γ-activated macrophages and $[NO]^b$ represents the NO concentration in supernatants from LPS/IFN-γ-activated control macrophages.

Gallic acid, Chlorogenic Acid. The inhibitory effect of gallic acid on NO production in LPS/IFN-γ-activated macrophages was dose-dependent (Table 7). The NO production decreased with the increase in concentration of gallic acid in the media. For example, the 250 and 500 µM gallic acid treatments attained 23 and 30% reduction in NO production, respectively without cytotoxicity toward the cells. Chlorogenic acid, although a very strong antioxidant in vitro (Table 6), showed no inhibitory effects on RAW 264.7 gamma (NO-) macrophages; instead, it induced production of NO (Table 7).

Cranberry and blueberry juice. Cranberry juice contains high levels of phenolic compounds (500 mg GAE/L). This concentration was increased dramatically after fermentation with the bacteria (≥3000 mg GAE/L). It was expected that fermented juice would demonstrate inhibitory activity on NO production in LPS/IFN-γ-activated macrophages. The inhibition on NO production by berry juices is shown in Table 7 and FIGS. 10 and 11. The unfermented blueberry juice exhibited a small effect (3.5%) on NO production but only at 500 µM concentration. Using fermented juice, a similar inhibitory effect was attained at 125 µM concentration. At high concentration (250 µM), blueberry juice exhibited a strong inhibition on NO production (40%) with slight toxicity on the macrophages. On the other hand, the unfermented cranberry juice had a significant effect on NO production (22%) at 125 µM without toxicity. The crude fermented cranberry juice attained an inhibition of 61% only at 31 µM. Higher concentrations of crude fermented cranberry juice had more inhibitory effects but they also increased the cytotoxicity on macrophages. The fermented cranberry juice after being adjusted showed less cytotoxicity while it still had a significant inhibitory effect 65% at 250 µM.

TABLE 7

Inhibition of macrophage NO production by berry juices and phenolic compounds

| Extract | Concentration (µM) | Nitrite (µM) | Cell viability (%) | Inhibitory effect (%) |
|---|---|---|---|---|
| Cranberry juice (unfermented) | Control | 0 | 100 (0.4) | |
| | LPS/IFN-γ | 30.6 (0.6) | 100 (0.8) | |
| | 16 | 29.6 (0.9) | 100.1 (2.8) | 5.1 (2.8) |
| | 31 | 27.5 (0.5) | 99.4 (6.5) | 10 (1.5) |
| | 63 | 25.6 (0.5) | 98.2 (2.7) | 16.3 (1.8) |
| | 125 | 23.7 (1.2) | 102.5 (3.2) | 22.2 (4) |
| | 250 | 16.7 (0.7) | 76.4 (7.5) | 45.4 (2.3) |
| | 500 | 0 | 18.9 (5.8) | |
| Cranberry juice (fermented and adjusted) | Control | 0 | 100 (1.2) | |
| | LPS/IFN-γ | 30.8 (0.6) | 100 (0.8) | |
| | 16 | 32.8 (0.8) | 101.6 (1.2) | 6.6 (1.8) |
| | 31 | 30.6 (0.8) | 98.7 (1.4) | 6.5 (2.5) |
| | 63 | 30.1 (0.3) | 98.2 (1.7) | 8.1 (0.9) |
| | 125 | 24.9 (1.5) | 95.1 (1.5) | 24 (4.6) |
| | 250 | 11.4 (0.4) | 92.9 (1.8) | 65 (1.2) |
| | 500 | 0 | 68.8 (6.5) | |
| Cranberry juice (fermented) | Control | 0 | 100 (0.3) | |
| | LPS/IFN-γ | 30.6 (0.6) | 100 (0.8) | |
| | 16 | 23.8 (0.9) | 93.9 (3.6) | 22.2 (3.1) |
| | 31 | 11.8 (0.4) | 95.8 (3.6) | 61.3 (1.2) |
| | 63 | 0.9 (0.3) | 86.3 (2.1) | 97.0 (1) |
| | 125 | 0 | 21.8 (3.6) | |
| | 250 | 0 | 1 (1.2) | |
| | 500 | 0 | 0 | |
| Blueberry juice (unfermented) | Control | 0 | 100 (0.4) | |
| | LPS/IFN-γ | 35.2 (0.6) | 100 (0.7) | |
| | 16 | 35.3 (0.2) | 103.3 (1) | 0 |
| | 31 | 37.0 (0.4) | 104.1 (0.9) | 0 |
| | 63 | 35.4 (1.2) | 100.8 (2.6) | 0 |
| | 125 | 37.7 (0.4) | 102.3 (2.8) | 0 |
| | 250 | 37.5 (1.7) | 97 (0.6) | 0 |
| | 500 | 33.9 (1.1) | 99.8 (2.9) | 3.5 (3.1) |
| Blueberry juice (fermented and adjusted) | Control | 0 | 100 (1.1) | |
| | LPS/IFN-γ | 36.3 (1.8) | 100 (0.3) | |
| | 16 | 40.1 (1.5) | 99.6 (0.8) | 0 |
| | 31 | 41.3 (0.6) | 99.3 (3.2) | 0 |
| | 63 | 37.7 (0.8) | 98.9 (3.3) | 0 |
| | 125 | 33.9 (0.8) | 99.3 (3.5) | 4.6 (1.5) |
| | 250 | 21.7 (0.3) | 93.8 (1.3) | 39.9 (0.4) |
| | 500 | 0.3 (0.5) | 52.6 (2.3) | 99.3 (1.3) |
| Gallic acid | Control | 0 | 100 (2.1) | |
| | LPS/IFN-γ | 32.7 (2) | 100 (7.7) | |
| | 16 | 36.2 (3.7) | 110 (2.2) | |
| | 31 | 35.4 (2.9) | 111 (6.4) | |
| | 63 | 29.3 (0.3) | 98.9 (0.9) | 10.5 (0.9) |
| | 125 | 31.1 (5.9) | 108.5 (0.6) | 19 (4.3) |
| | 250 | 25.2 (1.5) | 100.6 (3.7) | 23 (4.5) |
| | 500 | 22.6 (0.6) | 109.7 (5.4) | 30.9 (1.9) |

TABLE 7-continued

Inhibition of macrophage NO production by berry juices and phenolic compounds

| Extract | Concentration (μM) | Nitrite (μM) | Cell viability (%) | Inhibitory effect (%) |
|---|---|---|---|---|
| Chlorogenic acid | Control | 0 | 100 (3.2) | |
| | LPS/IFN-γ | 33.8 (1.8) | 100 (4.6) | |
| | 16 | 37.1 (0.4) | 102.4 (6.7) | −9.6 (1.3) |
| | 31 | 39 (1) | 105.6 (8.7) | −15.2 (2.9) |
| | 63 | 40.4 (1.64) | 106 (5.7) | −19.5 (4.9) |
| | 125 | 41.7 (1.7) | 98.5 (7.1) | −23.4 (5) |
| | 250 | 47.6 (1.4) | 102.3 (6.9) | −40.8 (4.2) |
| | 500 | 46.6 (1.5) | 102.8 (4.2) | −37.9 (4.5) |

TNF-α Quantification. Gallic acid and Chlorogenic acid may induce TNF-α production in LPS/IFN-γ-activated macrophages but not in a concentration dependant manner. This may explain the fermented berry juiced induced production of macrophage TNF-α, as the fermentation process with the bacterium produced gallic acid. Furthermore, chlorogenic acid represented a significant proportion of the blueberry juice phenolic content. However, only unfermented blueberry juice showed an inductive effect in a concentration-dependant manner, whereas unfermented cranberry juice or fermented blueberry and cranberry juice increased dramatically the production of TNF-α in LPS/IFN-γ-activated RAW 264.7 gamma NO(−) macrophages. The effect of gallic acid, chlorogenic acid, unfermented and fermented berry juices is shown Table 8.

TABLE 8

Induction of macrophage TNF-α production

| Extract | Concentration (μM) | TNF-α (%) | Cell viability (%) |
|---|---|---|---|
| Cranberry juice (unfermented) | Control | 2.9 (1.5) | 105.7 (1.8) |
| | LPS/IFN-γ | 100 (0.7) | 100 (1.3) |
| | 50 | 184 (5.8) | 101.1 (1.8) |
| | 100 | 179.5 (4.4) | 104.2 (0.9) |
| | 200 | 109.9 (7.4) | 92.8 (1.4) |
| | 300 | 73.02 (5) | 55.1 (4.9) |
| | 400 | 22.6 (2.8) | 49.6 (6.0) |
| | 500 | 15.3 (3.6) | 47.3 (6.4) |
| Cranberry juice (fermented and adjusted) | Control | 2.7 (2.7) | 105.7 (1.8) |
| | LPS/IFN-γ | 100 (3.6) | 100 (1.3) |
| | 50 | 359.1 (6.7) | 101.8 (3.2) |
| | 100 | 431.4 (19.3) | 106.3 (1.2) |
| | 200 | 465.8 (21.8) | 102.5 (4.1) |
| | 300 | 456.2 (20.5) | 99.8 (1.7) |
| | 400 | 448.8 (13.8) | 93.04 (3.2) |
| | 500 | 311.2 (13.8) | 88.1 (2.1) |
| Blueberry juice (unfermented) | Control | 6.1 (3.7) | 100 (0.4) |
| | LPS/IFN-γ | 100 (0.6) | 100 (2) |
| | 50 | 368.6 (8) | 98.8 (0.7) |
| | 100 | 432.8 (8.8) | 95.6 (2.2) |
| | 200 | 491.5 (36.4) | 100 (2.1) |
| | 300 | 502.7 (37.4) | 98.7 (0.6) |
| | 400 | 518.1 (20.9) | 99.1 (1.8) |
| | 500 | 666.9 (27.7) | 98.5 (1.8) |
| Blueberry juice (fermented and adjusted) | Control | 5.6 (3.6) | 100 (1.1) |
| | LPS/IFN-γ | 100 (7.5) | 100 (2.2) |
| | 50 | 779.7 (25.5) | 99.1 (0.9) |
| | 100 | 940.9 (33.8) | 97 (2.9) |
| | 200 | 1026.5 (9.8) | 100.7 (1.4) |
| | 300 | 1122.1 (8.3) | 97.7 (3.5) |
| | 400 | 1112.4 (4.9) | 100.5 (1.1) |
| | 500 | 907.9 (6.2) | 98.8 (1.7) |
| Gallic acid | Control | 7.6 (7) | 97.4 (5.1) |
| | LPS/IFN-γ | 100 (3.5) | 100 (0.5) |
| | 50 | 103.4 (3.2) | 97.7 (0.4) |
| | 100 | 126.2 (11) | 98.3 (2.3) |
| | 200 | 160.3 (8.4) | 96.7 (0.8) |

TABLE 8-continued

Induction of macrophage TNF-α production

| Extract | Concentration (μM) | TNF-α (%) | Cell viability (%) |
|---|---|---|---|
| | 300 | 257.4 (36.7) | 97.6 (2.5) |
| | 400 | 213.9 (54.8) | 96.1 (2.3) |
| | 500 | 183.5 (19.8) | 95.6 (1.6) |
| Chlorogenic acid | Control | 6.5 (3.3) | 100 (3.2) |
| | LPS/IFN-γ | 100 (15.3) | 100 (2.2) |
| | 50 | 105.7 (8.4) | 102 (0.4) |
| | 100 | 101.5 (5.4) | 100.6 (1.9) |
| | 200 | 99.2 (7.6) | 98.9 (2.3) |
| | 300 | 102.3 (15.6) | 97.1 (1.4) |
| | 400 | 126 (31.1) | 97.3 (1) |
| | 500 | 115.6 (15.4) | 99 (1.9) |

Example 5

Fermentation with Grapes

The ability of the bacterium (Accession No. 160103) to ferment a medium containing juice from green seedless grapes was assessed as described, above for blueberries and cranberries. The grapes used were President's choice Organics™ green seedless grapes, purchased from Loblaws Inc., Montreal. The results, as shown in Table 9 and FIG. 6B, indicate that fermentation with the bacterium can increase the total phenolic content of a medium comprising green grape juice. Red and black organic grapes can also be tested as described above for green grapes.

TABLE 9

Phenolic content during fermentation of green grapes by the bacterium.

| Extract | Time/day | Phenolic Concentration (mg GAE/L) |
|---|---|---|
| Unfermented green grapes | 0 | 133.7 (2.9) |
| | 1 | 126.7 (3.4) |
| | 2 | 128.6 (7.5) |
| | 3 | 123.2 (1.2) |
| | 4 | 128.1 (1.2) |
| | 5 | 131.9 (4.6) |
| Fermented green grapes | 0 | 135.3 (2.8) |
| | 1 | 172.1 (6.5) |
| | 2 | 297.3 (16.2) |
| | 3 | 401.0 (4.2) |
| | 4 | 442.3 (2.3) |
| | 5 | 512.6 (20.2) |

Example 6

Fermentation with Other Berries

Preliminary results have also indicated that the bacterium (Accession No. 160103) can be successfully fermented with media prepared using the following berries:

Elderberries (*Samucus canadensis*)

Chokecherry (*Prunus virginiana*)

Blackcurrant (*Ribes americanum* and/or *Ribes nigrum*).

The bacterium will also be tested for fermentation with Saskatoon berries. A mixture of Saskatoon berries from four different varieties will be used: Thiessen, Honeywood, Northline and Smokey varieties. The berries are hand-picked, cleaned of leaves, twigs, etc. and frozen within 24 hours of harvest. All the berries are from the Summer, 2003 crop.

Example 7

In Vivo Testing of the Antioxidant-Enriched Fermented Fruit Extracts

In order to investigate further the immunomodulatory effects of the fermented fruit extracts, the following in vivo tests can be conducted.

The effect of the fermented Suit extracts on tumoral and mucosal immunity can be investigated in BALB/c mice using protocols as described by Matar, C., et al., (*J. Dairy Res.* (2001) 68(4): 601-609). Mice will be fed the fermented fruit extract under investigation orally at days, 2, 5 and 7. The effect of antioxidants on the pathways leading to activation of NF-kB is well known. This effect can be measured by following the parameters of tumour growth over a 3 month period using standard techniques. The parameters to be followed are: 1) the rate of tumour development; 2) histopathological studies (haematoxin eosin stain); 3) apoptosis (Tunel method); 4) phagocytic index (PI) of peritoneal macrophages; 5) presence of specific cytokines for the NF-kB pathway, together with TNF-α, within the infiltrative tumour cells (mammalian or fibrosarcomas). In addition, the effect of the fermented fruit extract on the Gut Associated Lymphoid Tissues can be studied by measuring the ex vivo peritoneal macrophage activities in order to determine the effect on the pro-inflammatory cytokines profile.

The in vivo biological activity of the fermented fruit extracts can also be tested using animal models of diabetes or insulin resistance. In vitro bio-assays of insulin secretion and action can be used to complement these studies.

The in vivo biological activity of the fermented fruit extracts against free-radical and oxidative stress in the central nervous system can be tested in an appropriate animal model in order to assess the ability of the extracts to ameliorate neurodegenerative diseases, such as Alzheimer's, or conditions associated therewith.

The disclosure of all patents, publications, including published patent applications, and database entries referenced in this specification are specifically incorporated by reference in their entirety to the same extent as if each such individual patent, publication, and database entry were specifically and individually indicated to be incorporated by reference.

The embodiments of the invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. A biologically pure culture of a bacterial strain having all the identifying characteristics of the bacterium *Serratia vaccinii* deposited under International Depositary Authority of Canada (IDAC) Accession Number 160103.

2. A biologically pure culture of a bacterial strain having a 16S rRNA gene comprising a nucleotide sequence that is at least 99% identical to the sequence as set forth in SEQ ID NO:1, wherein said biologically pure culture is capable of fermenting fruit extracts to increase the antioxidant content thereof.

3. The biologically pure culture according to claim 2, wherein said 16S rRNA gene comprises a nucleotide sequence that is at least 99.5% identical to the sequence as set forth in SEQ ID NO:1.

4. A composition comprising an effective amount of the biologically pure culture according to claim 1, 2 or 3 to ferment fruit extracts to increase the antioxidant content thereof and a suitable medium or stabilizer.

5. The biologically pure culture according to claim 1, wherein said biologically pure culture is of the strain *Serratia vaccinii* deposited under IDAC Accession Number 160103.

6. The biologically pure culture according to claim 2, wherein said biologically pure culture does not ferment L-arabinose.

7. The composition according to claim 4, wherein said biologically pure culture is of the strain *Serratia vaccinii* deposited under IDAC Accession Number 160103.

8. An isolated bacterium having all the identifying characteristics of the bacterium *Serratia vaccinii* deposited under International Depositary Authority of Canada (IDAC) Accession Number 160103.

9. An isolated bacterium having a 16S rRNA gene comprising a nucleotide sequence that is at least 99% identical to the sequence as set forth in SEQ ID NO:1, wherein said bacterium is capable of fermenting fruit extracts to increase the antioxidant content thereof.

10. The isolated bacterium according to claim 9, wherein said 16S rRNA gene comprises a nucleotide sequence that is at least 99.5% identical to the sequence as set forth in SEQ ID NO:1.

* * * * *

SEQUENCE LISTING

```
<160> NUMBER OF SEQ ID NOS: 1

<210> SEQ ID NO 1
<211> LENGTH: 1535
<212> TYPE: DNA
<213> ORGANISM: Unknown
<220> FEATURE:
<223> OTHER INFORMATION: Accession No. 160103; Provisionally classified
      as Serratia vaccinii

<400> SEQUENCE: 1
tggagagttt gatcctggct cagattgaac gctggcggca ggcctaacac atgcaagtcg      60
agcggtagca cgggagagct tgctctctgg gtgacgagcg gcggacgggt gagtaatgtc     120
tgggaaactg cctgatggag ggggataact actggaaacg gtagctaata ccgcatgatg     180
tcgcaagacc aaagtggggg accttcgggc ctcacgccat cggatgtgcc cagatgggat     240
tagctagtag gtggggtaat ggctcaccta ggcgacgatc ctagctggtc tgagaggatg     300
accagccaca ctggaactga gacacggtcc agactcctac gggaggcagc agtggggaat     360
attgcacaat gggcgcaagc ctgatgcagc catgccgcgt gtgtgaagaa ggccttaggg     420
ttgtaaagca ctttcagcga ggaggaaggc gttgtagtta atagctgcaa cgattgacgt     480
tactcgcaga agaagcaccg gctaactccg tgccagcagc cgcggtaata cggagggtgc     540
aagcgttaat cggaattact gggcgtaaag cgcacgcagg cggtttgtta agtcagatgt     600
gaaatccccg agcttaactt gggaactgca tttgaaactg gcaagctaga gtcttgtaga     660 gggggtaga attccaggtg tagcggtgaa atgcgtagag atctggagga ataccggtgg     720
cgaaggcggc cccctggaca aagactgacg ctcaggtgcg aaagcgtggg gagcaaacag     780
gattagatac cctggtagtc cacgctgtaa acgatgtcga cttggaggtt gtgcccttga     840
ggcgtggctt ccggagctaa cgcgttaagt cgaccgcctg gggagtacgg ccgcaaggtt     900
aaaactcaaa tgaattgacg ggggcccgca caagcggtgg agcatgtggt ttaattcgat     960
```

```
gcaacgcgaa gaaccttacc tactcttgac atccagagaa tttgctagag atagcttagt    1020
gccttcggga actctgagac aggtgctgca tggctgtcgt cagctcgtgt tgtgaaatgt    1080
tgggttaagt cccgcaacga gcgcaaccct tatcctttgt tgccagcacg taaggtggga    1140
actcaaagga gactgccggt gataaaccgg aggaaggtgg ggatgacgtc aagtcatcat    1200
ggcccttacg agtagggcta cacacgtgct acaatggcgt atacaaagag aagcgaactc    1260
gcgagagcaa gcggacctca taaagtacgt cgtagtccgg attggagtct gcaactcgac    1320
tccatgaagt cggaatcgct agtaatcgta gatcagaatg ctacggtgaa tacgttcccg    1380
ggccttgtac acaccgcccg tcacaccatg ggagtgggtt gcaaaagaag taggtagctt    1440
aaccttcggg agggcgctta ccactttgtg attcatgact ggggtgaagt cgtaacaagg    1500
taaccgtagg ggaacctgcg gtggatcacc tcctt                              1535
```